(12) United States Patent
McCarthy et al.

(10) Patent No.: US 9,714,224 B2
(45) Date of Patent: Jul. 25, 2017

(54) HETEROCYCLIC COMPOUNDS AND METHODS OF THEIR USE

(71) Applicant: Novartis AG, Basel (CH)

(72) Inventors: Thomas David McCarthy, Old Greenwich, CT (US); Alan Naylor, Royston Hertfordshire (GB)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/903,166

(22) PCT Filed: Jul. 8, 2014

(86) PCT No.: PCT/AU2014/050116
§ 371 (c)(1),
(2) Date: Jan. 6, 2016

(87) PCT Pub. No.: WO2015/003223
PCT Pub. Date: Jan. 15, 2015

(65) Prior Publication Data
US 2016/0145213 A1 May 26, 2016

(30) Foreign Application Priority Data

Jul. 8, 2013 (AU) ................. 2013902513

(51) Int. Cl.
*C07D 217/26* (2006.01)
*A61K 31/44* (2006.01)
*C07H 13/10* (2006.01)
*C07H 13/04* (2006.01)
*C07H 17/02* (2006.01)

(52) U.S. Cl.
CPC ........... *C07D 217/26* (2013.01); *C07H 13/04* (2013.01); *C07H 13/10* (2013.01); *C07H 17/02* (2013.01)

(58) Field of Classification Search
None
See application file for complete search history.

(56) References Cited

U.S. PATENT DOCUMENTS

| 5,246,943 | A | 9/1993 | Blankley et al. |
| 2014/0378430 | A1 | 12/2014 | McCarthy et al. |
| 2015/0218180 | A1 | 8/2015 | McCarthy et al. |
| 2016/0257656 | A1 | 9/2016 | McCarthy et al. |

FOREIGN PATENT DOCUMENTS

| WO | WO03/041641 A2 | 5/2003 |
| WO | 2006/055951 A2 | 5/2006 |
| WO | 2007/106938 A1 | 9/2007 |
| WO | WO2011/088504 A1 | 7/2011 |
| WO | WO2012/010843 A1 | 1/2012 |

OTHER PUBLICATIONS

Voroshilova et al, Chemical Abstract 120:311212 of Zhurnal Nauchnoi i Prikladnoi Fotografii (1994), 39(1), 35-9.*
Vanatten et al.: "A novel series of selective, non-peptide inhibitors of angiotensin II binding to the AT2 site", Journal of Medicinal Chemistry, American Chemical Society, vol. 36, No. 25, (1993), pp. 3985-3992.
S Klutchko: "Tetrahydroisoquinoline derivatives with AT2-specific angiotensin II reception binding inhibitory activity", Bioorganic & Medicinal Chemistry Letters, vol. 4, No. 1, Jan. 6, 1994, pp. 57-62.

* cited by examiner

*Primary Examiner* — Zinna Northington Davis
(74) *Attorney, Agent, or Firm* — Sophie Binet Cross

(57) ABSTRACT

The present invention relates generally to compounds that are useful in antagonizing the angiotensin II type 2 ($AT_2$) receptor. More particularly, the invention relates to substituted isoquinoline compounds and their use as $AT_2$ receptor antagonists. Pharmaceutical compositions comprising the compounds and their use in modulating the $AT_2$ receptor and therapies that require modulation of the $AT_2$ receptor are described.

20 Claims, No Drawings

HETEROCYCLIC COMPOUNDS AND METHODS OF THEIR USE

FIELDS OF THE INVENTION

The present invention relates generally to compounds that are useful in antagonizing the angiotensin II type 2 ($AT_2$) receptor. More particularly, the invention relates to heterocyclic compounds of formula (I) and their use as $AT_2$ receptor antagonists. Pharmaceutical compositions comprising the compounds and their use in modulating the $AT_2$ receptor and therapies that require modulation of the $AT_2$ receptor are described.

BACKGROUND OF THE INVENTION

Although the $AT_2$ receptor has been known since the 1980s, much less is known about its biological function than the angiotensin II type 1 ($AT_1$) receptor, which has been studied for its functional effects on vasoconstriction, aldosterone release and cardiovascular growth [Wexler et al., 1996]. However, more recently the $AT_2$ receptor has been implicated in the differentiation and regeneration of neuronal tissue [Steckelings et al., 2005; Chakrabarty et al., 2008], cell proliferation and angiogenesis [Clere et al., 2010] and maintenance of bone mass [Izu et al., 2009].

$AT_2$ receptor antagonists have also recently been associated with the treatment of pain [Anand et al. 2012; Smith, Woodruff et al., 2013], particularly inflammatory pain [WO 2007/106938; Chakrabarty et al. 2013] and neuropathic pain [WO 2006/066361; Smith et al. 2013], two types of pain which are difficult to treat or relieve. Impaired nerve conduction velocity is also associated with nerve damage and has been implicated in peripheral neuropathies, Carpel Tunnel Syndrome, ulnar neuropathy, Guillian-Barré Syndrome, fascioscapulohumeral muscular dystrophy and spinal disc herneation. Impaired nerve conduction velocity can result in diminished reflex responses and altered peripheral sensation such as parathesia and in some cases pain and $AT_2$ receptor antagonists have been shown to restore nerve conduction velocity [WO 2011/088504].

While there are effective therapies for treating nociceptive pain, inflammatory and neuropathic pain are often resistant to these therapies. In addition, current therapies of neuropathic pain, inflammatory pain, impaired nerve conduction velocity and other types of pain that are difficult to treat, have serious side effects, for example, cognitive changes, sedation, nausea and in the case of narcotic drugs, tolerance and dependence. There is a need for further therapies that treat or prevent neuropathic pain, inflammatory pain, impaired nerve conduction velocity and other painful conditions that are currently difficult to treat.

Cell proliferation and angiogenesis are important biological functions in normal tissue. However, uncontrolled cell proliferation and angiogenesis can lead to tumors and other proliferative disorders. While there are some effective chemotherapies available for tumors, many result in unpleasant side effects and/or have high toxicity for normal cells. Further therapies for reducing or preventing abnormal cell proliferation in a controlled manner are required and $AT_2$ receptor antagonists have been shown to have antiproliferative activity [Clere et al., 2010].

Osteoporosis is a significant problem in older populations, especially in post-menopausal women. Current therapies for osteoporosis rely on calcium supplementation. However, the control of bone formation and bone resorption is complex and further therapies for improving bone mass are required and $AT_2$ receptor antagonists have been shown to increase bone mass [Izu et al., 2009].

The role of the $AT_2$ receptor in modulating neuronal outgrowth and associated effects of $AT_2$ receptor antagonists on reducing neuronal outgrowth, indicates that $AT_2$ receptor antagonists may be useful therapeutics in diseases characterized by aberrant nerve regeneration [Chakrabarty et al., 2008].

The present invention is predicated in part on the discovery of heterocyclic tetrahydroisoquinoline compounds that have $AT_2$ receptor antagonist activity.

SUMMARY OF THE INVENTION

In a first aspect of the present invention there is provided a compound of formula (I):

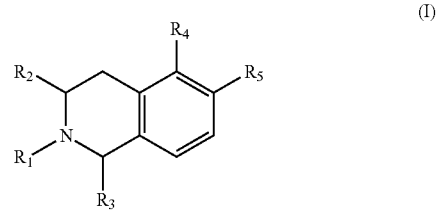

(I)

wherein $R_1$ is —C(=O)$CHR_6R_7$, —C(=O)$NR_6R_7$, —C(=O)$CH_2CHR_6R_7$, —C(=)CH=$CR_6R_7$, —C(=S)CH—$R_6R_7$, —C(=S)$NR_6R_7$, —C(=S)$CH_2CHR_6R_7$, —C(=S)CH=$CR_6R_7$, —C(=$NR_8$)$CHR_6R_7$, —C(=$NR_8$)$NR_6R_7$, —C(=$NR_8$)$CH_2CHR_6R_7$ and —C(=$NR_8$)CH=$CR_6R_7$;

one of $R_2$ and $R_3$ is hydrogen or oxo (=O) and the other is a carboxylic acid, —$CH_2CO_2H$, —C(=O)-2-glucuronic acid, —C(=O)C(=O)OH, —$CH_2OH$, —C(=O)$NH_2$, —$CH_2C$(=O)$NH_2$, —CN, —$CH_2CN$, a carboxylic acid bioisostere or a —$CH_2$-carboxylic acid bioisostere;

$R_4$ is hydrogen, $R_9$, —$C_{1-6}$alkyl$R_9$, —$C_{2-6}$alkenyl$R_9$, —$C_{2-6}$alkynyl$R_9$, —OH, —$OR_9$, —$OC_{1-6}$alkyl$R_9$, —$OC_{2-6}$alkenyl$R_9$, —$OC_{2-6}$alkynyl$R_9$, —NHC(=O)$R_9$, —NHC(O)$C_{1-6}$ alkyl$R_9$, —NHC(=)$C_{2-6}$alkenyl$R_9$, —NHC(=O)$C_{2-6}$alkynyl$R_9$, —NHC(=O)$NHR_9$, —NHC(=O)$NHC_{1-6}$alkyl$R_9$, —NHC(=)$NHC_{2-6}$alkenyl$R_9$, —NHC(=O)$NHC_{2-6}$alkynyl$R_9$, —NHC(=O)$OR_9$, —NHC(=O)$OC_{1-6}$alkyl$R_9$, —NHC(=O)$OC_{2-6}$alkenyl$R_9$, —NHC(=O)$OC_{2-6}$alkynyl$R_9$, —$NHSO_2R_9$, —$NHSO_2C_{1-6}$alkyl$R_9$, —$NHSO_2C_{2-6}$alkenyl$R_9$, —$NHSO_2C_{2-6}$alkynyl$R_9$, —$SO_2NHR_9$, —$SO_2NHC_{1-6}$alkyl$R_9$, —$SO_2NHC_{2-6}$alkenyl$R_9$, —$SO_2NHC_{2-6}$alkynyl$R_9$, —C(=O)$NHR_9$, —C(=O)$NHC_{1-6}$alkyl$R_9$, —C(=O)$NHC_{2-6}$alkenyl$R_9$, —C(=O)$NHC_{2-6}$alkynyl$R_9$, —C(=O)$R_9$, —C(=O)$C_{1-6}$alkyl$R_9$, —C(=O)$C_{2-6}$alkenyl$R_9$, —C(=O)$C_{2-6}$alkynyl$R_9$, —C(=O)$OR_9$, —C(=O)$OC_{1-6}$alkyl$R_9$, —C(=O)$OC_{2-6}$alkenyl$R_9$, —C(=O)$OC_{2-6}$alkynyl$R_9$, —C(=O)$NHR_9$, —C(=O)$NHC_{1-6}$alkyl$R_9$, —C(=O)$NHC_{2-6}$alkenyl$R_9$ or —C(=O)$NHC_{2-6}$alkynyl$R_9$;

$R_5$ is hydrogen, —OH, —$C_{1-6}$alkyl, —$OC_{1-6}$alkyl, —C($R_{10}$)$_3$, —OC($R_{10}$)$_3$, aryl, —$C_{1-6}$alkylaryl or —$OC_{1-6}$alkylaryl;

$R_6$ and $R_7$ are independently hydrogen, —$C_{1-6}$alkyl, cycloalkyl, cycloalkenyl, aryl, heterocyclyl, heteroaryl, —$CH_2$aryl, —$CH_2$cycloalkyl, —$CH_2$cycloalkenyl, —$CH_2$heterocyclyl or —$CH_2$heteroaryl; provided that $R_6$ and $R_7$ are not both hydrogen;

$R_8$ is hydrogen, —$C_{1-6}$alkyl, aryl or —$C_{1-6}$alkylaryl;
$R_9$ is cycloalkyl, cycloalkenyl, aryl, heterocyclyl or heteroaryl;
each $R_{10}$ is independently selected from the group consisting of hydrogen and halogen; and
wherein each alkyl, alkenyl, alkynyl, cycloalkyl, cycloalkenyl, aryl, heterocyclyl and heteroaryl may be optionally substituted;
or a pharmaceutically acceptable salt thereof;
provided that:
   (i) $R_4$ and $R_5$ are not both hydrogen; and
   (ii) when $R_2$ is —$CH_2OH$, $CO_2H$ or a carboxylic acid bioisostere and $R_4$ is hydrogen, phenyl, —Ophenyl, —$C_{1-4}$alkylphenyl or —$OC_{1-4}$alkylphenyl in which the alkyl group is unsubstituted, biphenyl, —Obiphenyl, naphthyl or —Onaphthyl, $R_5$ is not hydrogen, —$OC_{1-4}$ alkyl, phenyl, benzyl, naphthyl, biphenyl or —Oaryl.

In another aspect, the present invention provides a pharmaceutical composition comprising the compound of formula (I) or a pharmaceutically acceptable salt thereof and a pharmaceutically acceptable carrier.

In a further aspect of the invention, there is provided a method of treating or preventing neuropathic pain in a subject comprising administering a compound of formula (I) or a pharmaceutically acceptable salt thereof.

In yet a further aspect of the invention there is provided a method of treating or preventing a condition characterized by neuronal hypersensitivity in a subject comprising administering a compound of formula (I) or a pharmaceutically acceptable salt thereof.

In yet another aspect of the invention, there is provided a method of treating or preventing inflammatory pain in a subject comprising administering a compound of formula (I) or a pharmaceutically acceptable salt thereof.

In a further aspect, the present invention provides a method of treating or preventing impaired nerve conduction velocity in a subject comprising administering a compound of formula (I) or a pharmaceutically acceptable salt thereof.

In yet a further aspect of the invention there is provided a method of producing analgesia in a subject comprising administering a compound of formula (I) or a pharmaceutically acceptable salt thereof.

In still another aspect of the invention there is provided a method of treating or preventing a cell proliferative disorder in a subject comprising administering a compound of formula (I) or a pharmaceutically acceptable salt thereof.

In a further aspect the present invention provides a method of treating or preventing a disorder associated with an imbalance between bone resorption and bone formation in a subject comprising administering a compound of formula (I) or a pharmaceutically acceptable salt thereof.

In yet another aspect the present invention provides a method of treating a disorder associated with aberrant nerve regeneration in a subject comprising administering a compound of formula (I) or a pharmaceutically acceptable salt thereof.

DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

As used herein, the term "$AT_2$ receptor" means an angiotensin II type 2 ($AT_2$) receptor polypeptide that can bind angiotensin II and/or one or more other ligands. The term "$AT_2$ receptor" encompasses vertebrate homologs of $AT_2$ receptor family members, including, but not limited to, mammalian, reptilian and avian homologs. Representative mammalian homologs of $AT_2$ receptor family members include, but are not limited to, murine and human homologs.

The term "antagonist" as used herein refers to a compound that decreases or inhibits the biological activity and/or function of an $AT_2$ receptor, including binding to the $AT_2$ receptor and blocking access to angiotensin II, inhibiting a gene that expresses $AT_2$ receptor, or inhibiting an expression product of that gene. By the term "selective", is meant that the compound binds to and/or inhibits $AT_2$ receptor activity to a greater extent than binding and inhibition of the $AT_1$ receptor. In some instances, selective refers to binding and/or inhibition of the $AT_2$ receptor with little or no binding at the $AT_1$ receptor.

The term "allodynia" as used herein refers to the pain that results from a non-noxious stimulus i.e. pain due to a stimulus that does not normally provoke pain. Examples of allodynia include, but are not limited to, cold allodynia, tactile allodynia (pain due to light pressure or touch), and the like.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception", which is used in the art as a quantitative measure of analgesia or reduced pain sensitivity in animal models.

The term "anti-allodynia" is used herein to describe states of reduced pain perception, including absence from pain sensations as well as states of reduced or absent sensitivity to non-noxious stimuli. Such states of reduced or absent pain perception are induced by the administration of a pain-controlling agent or agents and occur without loss of consciousness, as is commonly understood in the art.

The term "causalgia" as used herein refers to the burning pain, allodynia, and hyperpathia after a traumatic nerve lesion, often combined with vasomotor and sudomotor dysfunction and later trophic changes.

By "complex regional pain syndromes" is meant the pain that includes, but is not limited to, reflex sympathetic dystrophy, causalgia, sympathetically maintained pain, and the like.

By "condition characterized by neuronal hypersensitivity" is meant conditions that have symptoms of pain related to neuronal hypersensitivity and/or allodynia. Examples of this type of condition include fibromyalgia and irritable bowel syndrome.

By "disorder associated with aberrant nerve regeneration" is meant disorders in which there is abnormal axon outgrowth in neurons. This abnormal outgrowth may be associated with painful conditions including breast pain, interstitial cystitis, vulvodynia and cancer chemotherapy-induced neuropathies.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "hyperalgesia" is meant an increased response to a stimulus that is normally painful. A hyperalgesia condition is one that is associated with pain caused by a stimulus that is not normally painful.

By "neuropathic pain" is meant any pain syndrome initiated or caused by a primary lesion or dysfunction in the peripheral or central nervous system. Examples of neuropathic pain include, but are not limited to, thermal or mechanical hyperalgesia, thermal or mechanical allodynia, diabetic pain, entrapment pain, and the like.

The term "nociceptive pain" refers to the normal, acute pain sensation evoked by activation of nociceptors located in non-damaged skin, viscera and other organs in the absence of sensitization.

As used herein "inflammatory pain" refers to pain induced by inflammation. Such types of pain may be acute or chronic and can be due to any number of conditions characterized by inflammation including, without limitation, burns including chemical, frictional or thermal burns, autoimmune diseases such as rheumatoid arthritis, osteoarthritis and inflammatory bowel disease including Crohn's disease and colitis, as well as other inflammatory diseases including carditis, dermatitis, myositis, neuritis and collagen vascular diseases.

The term "pain" as used herein is given its broadest sense and includes an unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, 28$^{th}$ Edition, W. B. Saunders Company, Philadelphia, Pa.). The goal of treatment of pain is to reduce the degree of severity of pain perceived by a treatment subject.

By the phrases "impaired NCV" or "impaired nerve conduction velocity" and the like is meant any nerve conduction demonstrably abnormal in any one of the parameters assessed for normal nerve signal conduction. Whether the various parameters of NCV are normal is typically an assessment made by the relevant trained clinician. General background, terminology and procedures known to those in the art for evaluating NCV are described in "Proper performance and interpretation of electrodiagnostic studies' Muscle Nerve. (2006) 33(3):436-439 and "Electrodiagnostic medicine listing of sensory, motor, and mixed nerves." Appendix J of Current Procedural Terminology (CPT) 2007, authored by The American Association of Neuromuscular & Electrodiagnostic Medicine and published by the American Medical Association. Impaired or abnormal nerve conduction velocity is a symptom of nerve dysfunction or damage and may be causal to or a symptom of a large number of diseases or disorders, particularly diseases or disorders that exhibit diminished reflex responses and altered peripheral sensation including parasthesia. As used herein, "paresthesia" refers to a sensation of tingling, prickling, weakness or numbness in a subject's skin. It is also known as "pins and needles" or a limb "falling asleep". Paresthesia may be transient, acute or chronic and may occur alone or be accompanied by other symptoms such as pain.

As used herein, the term "cell proliferative disorder" refers to diseases or conditions where unwanted or damaged cells are not removed by normal cellular process, or diseases or conditions in which cells undergo aberrant, unwanted or inappropriate proliferation. Disorders characterized by inappropriate cell proliferation include, for example, inflammatory conditions such as inflammation arising from acute tissue injury including, for example, acute lung injury, cancer including cancers characterized by tumors, autoimmune disorders, tissue hypertrophy and the like.

The term "disorder associated with an imbalance between bone resorption and bone formation" includes disorders where there is insufficient development of bone mass, excessive bone resorption and insufficient bone formation during remodelling. An exemplary disorder associated with an imbalance between bone resorption and bone formation is osteoporosis.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentyl, cyclohexyl, cycloheptyl and cyclooctyl.

As used herein, the term "cycloalkenyl" refers to an unsaturated cyclic hydrocarbon. The cycloalkenyl ring may include a specified number of carbon atoms. For example, a 5 to 8 membered cycloalkenyl group includes 5, 6, 7 or 8 carbon atoms. The cycloalkenyl group has one or more double bonds and when more than one double bond is present, the double bonds may be unconjugated or conjugated, however the cycloalkenyl group is not aromatic. Examples of suitable cycloalkenyl groups include, but are not limited to, cyclopentenyl, cyclohexenyl, cyclohexadienyl, cycloheptenyl, cycloheptadienyl, cycloheptatrienyl, cyclooctenyl, cyclooctadienyl and cyclooctatrienyl rings.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

The term "benzyl" where used herein refers to a phenylmethylene group, $C_6H_5CH_2$—.

As used herein, the term "halogen" or "halo" refers to fluorine (fluoro), chlorine (chloro), bromine (bromo) and iodine (iodo).

The term "heterocyclic" or "heterocyclyl" as used herein, refers to a cyclic hydrocarbon in which one to four carbon atoms have been replaced by heteroatoms independently selected from the group consisting of N, N(R), S, S(O), $S(O)_2$ and O. A heterocyclic ring may be saturated or unsaturated but not aromatic. A heterocyclic group may also be part of a spirocyclic group containing 1, 2 or 3 rings, two of which are in a "spiro" arrangement. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, thiophenyl, benzothienyl, benzofuranyl, benzodioxane, benzodioxin, quinolinyl, isoquinolinyl, oxazolyl, isoxazolyl, benzoxazolyl, imidazolyl, pyrazinyl, pyridazinyl, pyridinyl, pyrimidinyl, pyrrolyl, tetrahydroquinolinyl, thiazolyl, isothiazolyl, 1,2,3-triazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl, tetrazolyl, carbazolyl, xanthenyl, acridinyl, phenazinyl, phenothiazinyl, phenoxazinyl, azepinyl, oxepinyl and thiepinyl. Particular heteroaryl groups have 5- or 6-membered rings, such as pyrazolyl, furanyl, thienyl, oxazolyl, indolyl, isoindolyl, 1H,3H-1-oxoisoindolyl, isoxazolyl, benzoxazolyl, imidazolyl, pyrazinyl, pyridazinyl, pyridinyl, pyrimidinyl, pyrrolyl, thiazolyl, isothiazolyl, 1,2,3-triazolyl, 1,2,4-triazolyl and 1,2,4-oxadiazolyl and 1,2,4-thiadiazolyl.

Each alkyl, alkenyl, alkynyl, cycloalkyl, cycloalkenyl, aryl, heterocyclyl and heteroaryl whether an individual entity or as part of a larger entity may be optionally substituted with one or more optional substituents selected from the group consisting of $C_{1-6}$alkyl, $C_{2-6}$alkenyl, $C_{3-6}$cycloalkyl, oxo (=O), —OH, —SH, $C_{1-6}$alkylO—, $C_{2-6}$alkenylO—, $C_{3-6}$cycloalkylO—, $C_{1-6}$alkylS—, $C_{2-6}$alkenylS—, $C_{3-6}$cycloalkylS—, —$CO_2H$, —$CO_2C_{1-6}$alkyl, —$NH_2$, —NH($C_{1-6}$alkyl), —N($C_{1-6}$alkyl)$_2$, —NH(phenyl), —N(phenyl)$_2$, —N($C_{1-6}$alkyl)(phenyl), —CN, —$NO_2$, -halogen, —$CF_3$, —$OCF_3$, —$SCF_3$, —$CHF_2$, —$OCHF_2$, —$SCHF_2$, -phenyl, -heterocyclyl, -heteroaryl, —Oheteroaryl, —Oheterocyclyl, —Ophenyl, —C(O)phenyl and —C(O)$C_{1-6}$alkyl. Examples of suitable substituents include, but are not limited to, methyl ethyl, propyl, isopropyl, butyl, sec-butyl, ten-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, —$CO_2H$, —$CO_2CH_3$, trifluoromethyl, trifluoromethoxy, trifluoromethylthio, difluoromethyl, difluoromethoxy, difluoromethylthio, morpholino, amino, methylamino, dimethylamino, phenyl, phenoxy, phenylcarbonyl, benzyl and acetyl.

The term "carboxylic acid bioisotere" refers to a group which is physiochemically or topologically similar to carboxylic acid or carboxylate group. Examples of suitable carboxylic acid bioisosteres include, but are not limited to, tetrazole, tetrazolate, —CONH— tetrazole, oxadiazole, phosphate (—$PO_3H_2$), —C(OH)(CF$_3$)$_2$, alkylsulfonamides, N-(aryl or heteroaryl)-sulfonamides, acylsulfonamides and sulfonic acid (—$SO_3H$) [See Patani and LaVoie, 1996]. Examples of sulfonamide isosteric equivalents of carboxy groups include —C(=O)NHSO$_2$R$^a$, —C(=O)NHSO$_2$N(R$^a$)$_2$, —C(=O)NHSO$_2$NH(R$^a$), —SO$_2$NHC(=O)R$^a$, —SO$_2$NHC(=O)NHR$^a$, —SO$_2$NHR$^a$ and —NHSO$_2$R$^a$, where R$^a$ is selected from the group consisting of $C_{1-6}$alkyl, $C_{2-6}$alkenyl, $C_{3-8}$cycloalkyl, aryl, heterocyclyl, heteroaryl, —$CF_3$ and —$CHF_2$.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, toluenesulphonic, benezenesulphonic, salicylic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution. The compounds of the invention may exist as geometric isomers. The invention also relates to compounds in substantially pure cis (Z) or trans (E) or mixtures thereof.

COMPOUNDS OF THE INVENTION

In a first aspect of the present invention there is provided a compound of formula (I):

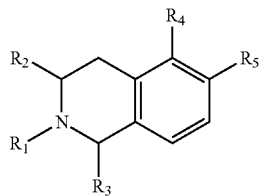

(I)

wherein $R_1$ is —C(=O)CHR$_6$R$_7$, —C(=O)NR$_6$R$_7$, —C(=O)CH$_2$CHR$_6$R$_7$, —C(=O)CH=CR$_6$R$_7$, —C(=S)CHR$_6$R$_7$, —C(=S)NR$_6$R$_7$, —C(=S)CH$_2$CHR$_6$R$_7$, —C(=S)CH=CR$_6$R$_7$, —C(=NR$_8$)CHR$_6$R$_7$, —C(=NR$_8$)NR$_6$R$_7$, —C(=NR$_8$)CH$_2$CHR$_6$R$_7$ and —C(=NR$_8$)CH=CR$_6$R$_7$;

one of $R_2$ and $R_3$ is hydrogen or oxo (=O) and the other is a carboxylic acid, —CH$_2$CO$_2$H, —C(=O)-2-glucuronic acid, —C(=O)C(=O)OH, —CH$_2$OH, —C(=O)NH$_2$, —CH$_2$C(=O)NH$_2$, —CN, —CH$_2$CN, a carboxylic acid bioisostere or a —CH$_2$-carboxylic acid bioisostere;

$R_4$ is hydrogen, $R_9$, —C$_{1-6}$alkylR$_9$, —C$_{2-6}$alkenylR$_9$, —C$_{2-6}$alkynylR$_9$, —OH, —OR$_9$, —OC$_{1-6}$ alkylR$_9$, —OC$_{2-6}$alkenylR$_9$, —OC$_{2-6}$alkynylR$_9$, —NHC(=O)R$_9$, —NHC(=O)C$_{1-6}$alkylR$_9$, —NHC(=O)C$_{2-6}$alkenylR$_9$, —NHC(=O)C$_{2-6}$ alkynylR$_9$, —NHC(=O)NHR$_9$, —NHC(=O)NHC$_{1-6}$alkylR$_9$, —NHC(=O)NHC$_{2-6}$alkenylR$_9$, —NHC(=O)NHC$_{2-6}$alkynylR$_9$, —NHC(=O)OR$_9$, —NHC(=O)OC$_{1-6}$alkylR$_9$, —NHC(=O)OC$_{2-6}$alkenylR$_9$, —NHC(=O)OC$_{2-6}$alkynylR$_9$, —NHSO$_2$R$_9$, —NHSO$_2$C$_{1-6}$alkylR$_9$, —NHSO$_2$C$_{2-6}$alkenylR$_9$, —NHSO$_2$C$_{2-6}$alkynylR$_9$, —SO$_2$NHR$_9$, —SO$_2$NHC$_{1-6}$alkylR$_9$, —SO$_2$NHC$_{2-6}$alkenylR$_9$, —SO$_2$NHC$_{2-6}$alkynylR$_9$, —C(=O)NHR$_9$, —C(=O)NHC$_{1-6}$alkylR$_9$, —C(=O)NHC$_{2-6}$alkenylR$_9$, —C(=O)NHC$_{2-6}$alkynylR$_9$, —C(=O)R$_9$, —C(=O)C$_{1-6}$alkylR$_9$, —C(=O)C$_{2-6}$alkenylR$_9$, —C(=O)C$_{2-6}$alkynylR$_9$, —C(=O)OR$_9$, —C(=O)OC$_{1-6}$alkylR$_9$, —C(=O)OC$_{2-6}$alkenylR$_9$, —C(=O)OC$_{2-6}$alkynylR$_9$, —C(=O)NHR$_9$, —C(=O)NHC$_{1-6}$alkylR$_9$, —C(=O)NHC$_{2-6}$alkenylR$_9$ or —C(=O)NHC$_{2-6}$alkynylR$_9$;

$R_5$ is hydrogen, —OH, —C$_{1-6}$alkyl, —OC$_{1-6}$alkyl, —C(R$_{10}$)$_3$, —OC(R$_{10}$)$_3$, aryl, —C$_{1-6}$alkylaryl or —OC$_{1-6}$alkylaryl;

$R_6$ and $R_7$ are independently hydrogen, —C$_{1-6}$alkyl, cycloalkyl, cycloalkenyl, aryl, heterocyclyl, heteroaryl, —CH$_2$aryl, —CH$_2$cycloalkyl, —CH$_2$cycloalkenyl, —CH$_2$heterocyclyl or —CH$_2$heteroaryl; provided that $R_6$ and $R_7$ are not both hydrogen;

$R_8$ is hydrogen, —C$_{1-6}$alkyl, aryl or —C$_{1-6}$alkylaryl;

$R_9$ is cycloalkyl, cycloalkenyl, aryl, heterocyclyl or heteroaryl;

each $R_{10}$ is independently selected from the group consisting of hydrogen and halogen; and wherein each alkyl, alkenyl, alkynyl, cycloalkyl, cycloalkenyl, aryl, heterocyclyl and heteroaryl may be optionally substituted;

or a pharmaceutically acceptable salt thereof;

provided that:

(iii) $R_4$ and $R_5$ are not both hydrogen; and (iv) when $R_2$ is —CH$_2$OH, CO$_2$H or a carboxylic acid bioisostere and $R_4$ is hydrogen, phenyl, —Ophenyl, —C$_{1-4}$alkylphenyl or —OC$_{1-4}$alkylphenyl in which the alkyl group is unsubstituted, biphenyl, —Obiphenyl, naphthyl or —Onaphthyl, $R_5$ is not hydrogen, —OC$_{1-6}$alkyl, phenyl, benzyl, naphthyl, biphenyl or —Oaryl.

In particular embodiments of formula (I), one or more of the following applies:

$R^1$ is —C(=O)CHR$^6$R$^7$, —C(=O)NR$^6$R$^7$, especially —C(=O)CH(aryl)(aryl), —C(=O)CH(aryl)(cycloalkyl), —C(=O)CH(cycloalkyl)(cycloalkyl), —C(=O)CH(aryl)(alkyl), —C(=O)N(aryl)(aryl), —C(=O)N(aryl)(cycloalkyl), —C(=O)N(cycloalkyl)(cycloalkyl) or —C(=O)N(aryl)(alkyl), where each aryl or cycloalkyl group is optionally substituted; more especially —C(=O)CH(phenyl)(phenyl), —C(=O)CH(phenyl)(cyclohexyl), —C(=O)N(phenyl)(phenyl) or —C(=O)N(phenyl)(cyclohexyl), wherein each phenyl or cyclohexyl group is optionally substituted with one or more substituents selected from —C$_{1-3}$alkyl, —OC$_{1-3}$alkyl and halo, especially methyl, methoxy and fluoro; most especially where $R^1$ is —C(=O)CH(phenyl)(phenyl) and —C(=O)N(phenyl)(phenyl);

one of $R^2$ and $R^3$ is hydrogen and the other is —CO$_2$H, —CH$_2$CO$_2$H, —C(=O)-2-glucuronic acid, —C(=O)C(=O)OH, —C(=O)NHSO$_2$C$_{1-6}$alkyl, —C(=O)NHSO$_2$phenyl, —C(=O)NHSO$_2$CF$_3$, —C(=O)NHSO$_2$N(C$_{1-6}$alkyl)$_2$, —C(=O)NHSO$_2$NH(C$_{1-6}$alkyl), —C(=O)NHSO$_2$N(CF$_3$)$_2$, —C(=O)NHSO$_2$NH(CF$_3$), —SO$_3$H or —PO$_3$H$_2$, especially —CO$_2$H, —CH$_2$CO$_2$H, —C(=O)NHSO$_2$C$_{1-4}$alkyl, —C(=O)NHSO$_2$phenyl, —C(=O)NHSO$_2$CF$_3$, —C(=O)NHSO$_2$N(C$_{1-4}$alkyl)$_2$ or —C(=O)NHSO$_2$N(CF$_3$)$_2$, more especially —CO$_2$H; especially where $R^3$ is hydrogen and $R^2$ is —CO$_2$H, —CH$_2$CO$_2$H, —C(=O)C(=O)OH, —C(=O)NHSO$_2$C$_{1-6}$alkyl, —C(=O)NHSO$_2$phenyl, —C(=O)NHSO$_2$CF$_3$, —C(=O)NHSO$_2$N(C$_{1-6}$alkyl)$_2$, —C(=O)NHSO$_2$NH(C$_{1-6}$alkyl), —C(=O)NHSO$_2$N(CF$_3$)$_2$, —C(=O)NHSO$_2$NH(CF$_3$), —SO$_3$H or —PO$_3$H$_2$, especially —CO$_2$H, —CH$_2$CO$_2$H, —C(=O)NHSO$_2$C$_{1-4}$alkyl, —C(=O)NHSO$_2$phenyl, —C(=O)NHSO$_2$CF$_3$, —C(=O)NHSO$_2$N(C$_{1-4}$alkyl)$_2$ or —C(=O)NHSO$_2$N(CF$_3$)$_2$, more especially $R_3$ is hydrogen and $R_2$ is —CO$_2$H; or $R^3$ is hydrogen or oxo and $R^2$ is —CH$_2$CO$_2$H, —C(=O)C(=O)OH or a carboxylic acid bioisostere, especially —CH$_2$CO$_2$H, a sulfonamide or C(=O)-2-glucuronic acid. Particular sulfonamides include —CONHSO$_2$C$_{1-6}$alkyl, —CONHSO$_2$aryl, —CONHSO$_2$C(R$_{10}$)$_3$, —C(=O)NHSO$_2$N(C$_{1-6}$alkyl)$_2$, —C(=O)NHSO$_2$NH(C$_{1-6}$alkyl), —C(=O)NHSO$_2$N(CF$_3$)$_2$, —C(=O)NHSO$_2$NH(CF$_3$), including —CONHSO$_2$CH$_3$, —CONHSO$_2$CH$_2$CH$_3$, —CONHSO$_2$CH$_2$CH$_2$CH$_3$, —CONHSO$_2$CH$_2$CH$_2$CH$_2$CH$_3$, —CONHSO$_2$CF$_3$, —CONHSO$_2$CHF$_2$, —CONHSO$_2$phenyl-C(=O)NHSO$_2$N(CH$_3$)$_2$ and —C(=O)NHSO$_2$N(CF$_3$)$_2$.

$R_4$ is —OH, aryl, heterocyclyl, heteroaryl, —C$_{1-6}$alkylaryl, —OC$_{1-6}$alkylaryl, —C$_{2-6}$alkenylaryl, —OC$_{2-6}$alkenylaryl, —C$_{2-6}$alkynylaryl, —OC$_{2-6}$alkynylaryl, —SO$_2$NHaryl, —SO$_2$NHC$_{1-6}$alkylaryl, —SO$_2$NHC$_{2-6}$alkenylaryl, —SO$_2$NHC$_{2-6}$alkynylaryl, —NHSO$_2$aryl-NHSO$_2$C$_{1-6}$alkylaryl, —NHSO$_2$C$_{2-6}$alkenylaryl, —NHSO$_2$C$_{2-6}$alkynylaryl, —NHC(=O)NHaryl, —NHC(=O)NHC$_{1-6}$alkylaryl, —NHC(=O)NHC$_{2-6}$alkenylaryl, —NHC(=O)NHC$_{2-6}$alkynylaryl, —NHCO$_2$aryl, —NHCO$_2$C$_{1-6}$alkylaryl, —NHCO$_2$C$_{2-6}$alkenylaryl, —NHCO$_2$C$_{2-6}$alkynylaryl, each of which may be optionally substituted; especially —OH, phenyl, benzoxazole, 4-phenyloxazole, 1-piperidine, 4-phenyl-1-piperidine, —C$_{1-6}$alkylphenyl, —OC$_{1-6}$alkylphenyl, —C$_{2-6}$alkenylphenyl, —OC$_{2-6}$alkenylphenyl, —C$_{2-6}$alkynylphenyl, —OC$_{2-6}$alkynylphenyl, —SO$_2$NHphenyl, —SO$_2$NHC$_{1-6}$alkylphenyl, —SO$_2$NHC$_{2-6}$alkenylphenyl, —SO$_2$NHC$_{2-6}$ alkynylphenyl, —NHSO$_2$phenyl-NHSO$_2$C$_{1-6}$alkylphenyl, —NHSO$_2$C$_{2-6}$alkenylphenyl, —NHSO$_2$C$_{2-6}$alkynylphenyl, —NHC(=O)NHphenyl, —NHC(=O)NHC$_{1-6}$alkylphenyl, —NHC(=O)NHC$_{2-6}$alkenylphenyl, —NHC(=O)NHC$_{2-6}$alkynylphenyl, —NHCO$_2$phenyl, —NHCO$_2$C$_{1-6}$alkylphenyl, —NHCO$_2$C$_{2-6}$alkenylphenyl, —NHCO$_2$C$_{2-6}$alkynylphenyl; more especially —OH, phenyl, benzoxazole, 4-phenyloxazole, 4-phenyl-1-piperidine, —C$_{1-3}$alkylphenyl, —OC$_{1-3}$alkylphenyl, —C$_{2-3}$alkenylphenyl, —OC$_{2-3}$alkenylphenyl, —C$_{2-3}$alkynylphenyl, —OC$_{2-3}$alkynylphenyl, —SO$_2$NHphenyl, —SO$_2$NHC$_{1-3}$alkylphenyl, —SO$_2$NHC$_{2-3}$alkenylphenyl, —SO$_2$NHC$_{2-3}$alkynylphenyl, —NHSO$_2$phenyl-NHSO$_2$C$_{1-3}$alkylphenyl, —NHSO$_2$C$_{2-3}$alkenylphenyl, —NHSO$_2$C$_{2-3}$alkynylphenyl, —NHC(=O)NHphenyl, —NHC(=O)NHC$_{1-3}$alkylphenyl, —NHC(=O)NHC$_{2-3}$alkenylphenyl, —NHC(=O)NHC$_{2-3}$alkynylphenyl, —NHCO$_2$phenyl, —NHCO$_2$C$_{1-3}$alkylphenyl, —NHCO$_2$C$_{2-3}$alkenylphenyl or —NHCO$_2$C$_{2-3}$alkynylphenyl;

$R_5$ is hydrogen, —OH, —OC$_{1-6}$alkyl or —OC(R$_{10}$)$_3$; especially —OH, —OC$_{1-6}$alkyl or OC(R$_{10}$)$_3$, more especially —OH, —OC$_{1-3}$alkyl, —OCF$_3$ or —OCHF$_2$; most especially —OH, —OCH$_3$, —OCF$_3$ or —OCHF$_2$;

$R^6$ and $R^7$ are independently selected from phenyl and cyclohexyl, especially where both $R^6$ and $R^7$ are phenyl; and $R^8$ is hydrogen, methyl, ethyl or phenyl.

In some embodiments, especially when $R^2$ a carboxylic acid, —CH$_2$CO$_2$H, —C(=O)-2-glucuronic acid, —C(=O)C(=O)OH, —CH$_2$OH, —C(=O)NH$_2$, —CH$_2$C(=O)NH$_2$, —CN, —CH$_2$CN, a carboxylic acid bioisostere or a —CH$_2$-carboxylic acid bioisostere; $R^2$ has an S stereochemistry.

In some embodiments, $R^4$ is not —C$_{1-6}$alkylaryl or —OC$_{1-6}$alkylaryl. In some embodiments, $R^5$ is not —OC$_{1-6}$alkyl.

In some embodiments, when $R_4$ is hydrogen, $R_2$ is hydrogen and $R_3$ is a carboxylic acid, —CH$_2$CO$_2$H, —C(=O)-2-glucuronic acid, —C(=O)C(=O)OH, —CH$_2$OH, —C(=O)NH$_2$, —CH$_2$C(=O)NH$_2$, —CN, —CH$_2$CN, a carboxylic acid bioisostere or a —CH$_2$-carboxylic acid bioisostere;

Particular compounds of formula (II) are:

| Compound | R$^1$ | R$^2$ | R$^3$ | R$^4$ | R$^5$ |
|---|---|---|---|---|---|
| 1 | —C(O)CH(phenyl)$_2$ | —CO$_2$H | H | —OCH$_2$Ph | —OCF$_3$ |
| 2 | —C(O)CH(phenyl)$_2$ | —CO$_2$H | H | —CH=CHPh (trans) | —OCH$_3$ |
| 3 | —C(O)CH(phenyl)$_2$ | —CO$_2$H | H | —CHOHCHOHPh | —OCH$_3$ |
| 4 | —C(O)CH(phenyl)$_2$ | —CO$_2$H | H | —CH=CHPh (trans) | H |
| 5 | —C(O)CH(phenyl)$_2$ | —CO$_2$H | H | —CHOHCHOHPh | H |
| 6 | —C(O)CH(phenyl)$_2$ | —CO$_2$H | H | —CH=CHPh (trans) | —OCF$_3$ |
| 7 | —C(O)CH(phenyl)$_2$ | —CO$_2$H | H | —CH$_2$CH$_2$Ph | —OCF$_3$ |
| 8 | —C(O)CH(phenyl)$_2$ | —CO$_2$H | H | —CHOHCHOHPh | —OCF$_3$ |
| 9 | —C(O)CH(phenyl)$_2$ | —CO$_2$H | H | —OCH$_2$Ph | —CHF$_2$ |
| 10 | —C(O)CH(phenyl)$_2$ | —CO$_2$H | H | —OCH$_2$Ph | —OCHF$_2$ |
| 11 | —C(O)CH(phenyl)$_2$ | —CONHSO$_2$CH$_3$ | H | —OCH$_2$Ph | —OCH$_3$ |
| 12 | —C(O)CH(phenyl)$_2$ | —CH$_2$CO$_2$H | H | —OCH$_2$Ph | —OCH$_3$ |
| 13 | —C(O)CH(phenyl)$_2$ | —CONHSO$_2$CH$_3$ | H | —OCH$_2$Ph | —OCF$_3$ |
| 14 | —C(O)CH(phenyl)$_2$ | —CH$_2$CO$_2$H | H | —OCH$_2$Ph | —OCF$_3$ |
| 15 | —C(O)CH(phenyl)$_2$ | —CO$_2$H | H | —C≡CPh | —OCH$_3$ |
| 16 | —C(O)CH(phenyl)$_2$ | —CO$_2$H | H | —C≡CPh | —OCF$_3$ |
| 17 | —C(O)CH(phenyl)$_2$ | —CO$_2$H | H | —C≡CPh | —OCHF$_2$ |
| 18 | —C(O)CH(phenyl)$_2$ | —CH$_2$CO$_2$H | H | —CHOHCHOHPh | —OCF$_3$ |
| 19 | —C(O)CH(phenyl)$_2$ | —CONHSO$_2$CH$_3$ | H | —C≡CPh | —OCHF$_2$ |
| 20 | —C(O)CH(phenyl)$_2$ | —CO$_2$H | H | —SO$_2$NHPh | —OCH$_3$ |
| 21 | —C(O)CH(phenyl)$_2$ | —CO$_2$H | H | —NHSO$_2$Ph | —OCH$_3$ |
| 22 | —C(O)CH(phenyl)$_2$ | —CO$_2$H | H | —NHCONHPh | —OCH$_3$ |
| 23 | —C(O)CH(phenyl)$_2$ | —CO$_2$H | H | —NHCO$_2$Ph | —OCH$_3$ |
| 24 | —C(O)CH(phenyl)$_2$ | —CONHSO$_2$CF$_3$ | H | —OCH$_2$Ph | —OCH$_3$ |
| 25 | —C(O)CH(phenyl)$_2$ | —CONHSO$_2$C$_4$H$_9$ | H | —OCH$_2$Ph | —OCH$_3$ |
| 26 | —C(O)CH(phenyl)$_2$ | —CONHSO$_2$Ph | H | —OCH$_2$Ph | —OCH$_3$ |
| 27 | —C(O)CH(phenyl)$_2$ | —CONHSO$_2$CF$_3$ | H | —OCH$_2$Ph | —OCF$_3$ |
| 28 | —C(O)CH(phenyl)$_2$ | —CONHSO$_2$C$_4$H$_9$ | H | —OCH$_2$Ph | —OCF$_3$ |
| 29 | —C(O)CH(phenyl)$_2$ | —CONHSO$_2$Ph | H | —OCH$_2$Ph | —OCF$_3$ |
| 30 | —C(O)CH(phenyl)$_2$ | —CONHSO$_2$CF$_3$ | H | —C≡CPh | —OCHF$_2$ |
| 31 | —C(O)CH(phenyl)$_2$ | —CONHSO$_2$C$_4$H$_9$ | H | —C≡CPh | —OCHF$_2$ |
| 32 | —C(O)CH(phenyl)$_2$ | —CONHSO$_2$Ph | H | —C≡CPh | —OCHF$_2$ |
| 33 | —C(O)CH(phenyl)$_2$ | (2-glucuronic acid ester) | H | —OCH$_2$Ph | —OCH$_3$ |
| 34 | —C(O)CH(phenyl)$_2$ | —CO$_2$H | H | —OCH$_2$Ph | —OH |
| 35 | —C(O)CH(phenyl)$_2$ | —CO$_2$H | =O | —OCH$_2$Ph | H |

-continued

| Compound | R¹ | R² | R³ | R⁴ | R⁵ |
|---|---|---|---|---|---|
| 36 | —C(O)CH(phenyl)₂ | —CO₂H | H | (benzoxazol-2-ylmethyl) | H |
| 37 | —C(O)CH(phenyl)₂ | H | —CO₂H | H | —Ph |
| 38 | —C(O)CH(phenyl)₂ | H | —CO₂H | H | —CH₂Ph |
| 39 | —C(O)CH(phenyl)₂ | —CO₂H | H | (4-phenyl-2,3-dihydrooxazol-2-yl) | H |
| 40 | —C(O)CH(phenyl)₂ | —C(=O)NHSO₂N(CH₃)₂ | H | —OCH₂Ph | —OCH₃ |
| 41 | —C(O)CH(phenyl)₂ | —C(=O)NHSO₂N(CH₃)₂ | H | —OH | —OCH₃ |
| 42 | —C(O)CH(phenyl)₂ | —C(=O)NHSO₂N(CH₃)₂ | H | —C≡CPh | —OCH₃ |
| 43 | —C(O)CH(phenyl)₂ | —C(=O)NHSO₂N(CH₃)₂ | H | —CH₂CH₂Ph | —OCH₃ |
| 44 | —C(O)CH(phenyl)₂ | —C(=O)NHSO₂N(CH₃)₂ | H | (4-phenylpiperidin-1-yl) | —OCH₃ |
| 45 | —C(O)CH(phenyl)₂ | —C(=O)NHSO₂N(CH₃)₂ | H | (4-phenylpiperidin-1-yl) | —OCH₃ |
| 46 | —C(O)CH(phenyl)₂ | —CO₂H | H | (4-phenylpiperidin-1-yl) | —OCH₃ |
| 47 | —C(O)CH(phenyl)₂ | —CO₂H | H | (4-phenylpiperidin-1-yl) | —OCH₃ |
| 48 | —C(O)CH(phenyl)₂ | —C(=O)NHSO₂N(CH₃)₂ | H | —OCH₂C≡CPh | —OCH₃ |
| 49 | —C(O)CH(phenyl)₂ | —C(=O)NHSO₂N(CH₃)₂ | H | —OCH₂C≡C—4-F—Ph | —OCH₃ |
| 50 | —C(O)CH(phenyl)₂ | —CO₂H | H | —OCH₂C≡CPh | —OCH₃ |
| 51 | —C(O)CH(phenyl)₂ | —CO₂H | H | —OCH₂C≡C—4-F—Ph | —OCH₃ |

Particular compounds of formula (I) include compounds 33, 34, 40, 41, 48, 49, 50 and 51, especially 33, 34, 40, 48, 49, 50 and 51, more especially 34, 40, 48 and 50.

In some embodiments, the compounds of formula (I) are selective $AT_2$ receptor antagonists. In particular embodiments, the selective $AT_2$ receptor antagonists have an $IC_{50}$ at the $AT_2$ receptor of ≤100 nM and an $IC_{50}$ at the $AT_1$ receptor of >100,000 nM (10 μM) using the assay methodologies described in the Biological Examples.

The compounds of the invention are made by methods known in the art from commercially available starting materials and by methods known in the art. For Example, a suitable 2,3-disubstituted benzaldehyde such as 2,3-dihydroxybenzaldehyde may be functionalized to provide suitable substituents for $R_4$ and $R_5$ as shown in Scheme 1:

Scheme 1

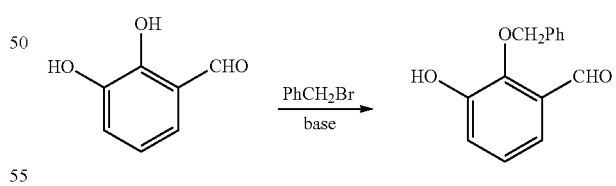

For example, reaction of the 2-hydroxy group with an arylalkylhalide such as benzylbromide, in the presence of a mild base such as $Na_2CO_3$ or $K_2CO_3$ in a polar solvent such as methanol or ethanol or acetone provides the disubstituted benzaldehyde.

The aldehyde is then condensed with hydantoin under mildly acidic conditions and subject to reduction as described in U.S. Pat. No. 5,246,943 and shown in Scheme 2:

Scheme 2

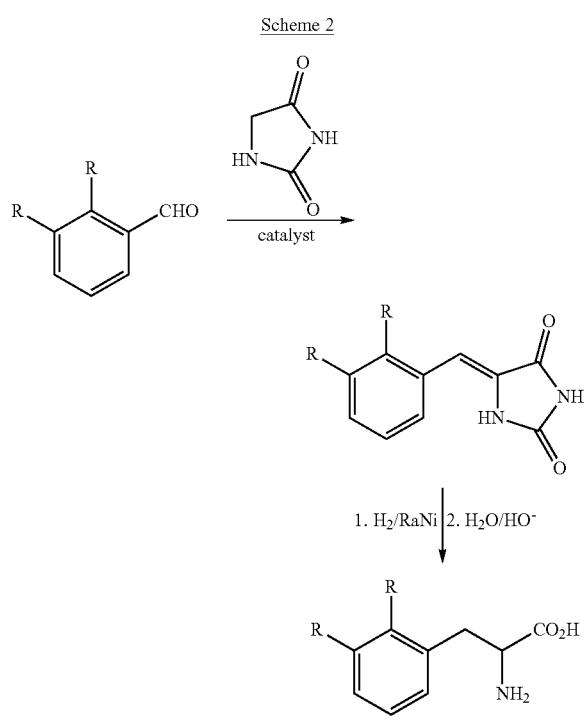

Another option is the use of the Horner-Wadsworth-Emmons reaction where the aldehyde is reacted with a stabilized phosphonate carbanion, followed by asymmetric reduction using a catalyst. Disubstituted phenylalanine derivatives may be prepared by asymmetric synthesis, for example, by the methods of Burk et al., 1993.

The phenylalanine derivative may be cyclized to a tetrahydroisoquinoline using Pictet-Spengler reaction as described in U.S. Pat. No. 5,246,943 and shown in Scheme 3:

Scheme 3

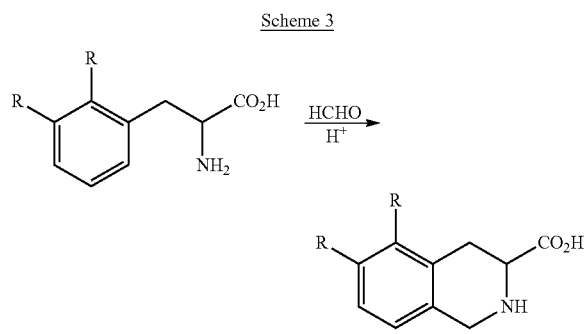

$R^1$ may be introduced by amide formation with a suitable carboxylic acid and the ring nitrogen. Amide formation is well known in the art and may involve the activation of the carboxylic acid, for example, the carboxy group is activated by formation of an acid chloride, carbodiimide, triazole or a uronium or phosphonium salt of a non-nucleophilic anion. Suitable activating groups are well known in the art including dicyclohexylcarbodiimide (DCC), diisopropylcarbodiimide (DIC), 1-ethyl-3-(dimethylaminopropyl)carbodiimide (EDCl), 1-hydroxybenzotriazole (HOBt), 1-hydroxy-7-azabenzotriazole (HOAt), ethyl-2-cyano-2-(hydroxyimino)acetate (Oxyma Pure), O-benzotriazole-N,N,N',N'-tetramethyluronium hexafluorophosphate (HBTU). O-(7-azabenzotriazol-1-yl)-N,N,N',N'-tetramethyluronium hexafluorophosphate (HATU), O-(6-chloro-1H-benzotriazol-1-yl)-1,1,3,3-tetramethyluronium tetrafluorophosphate (HCTU). O-benzotriazol-1-yl-N,N,N'N'-tetramethyluronium tetrafluorborate (TBTU), (benzotriazol-1-yloxy)tripyrrolidinophosphonium hexafluorophosphate (PyBOP); (benzotriazol-1-yloxy)-tris-(dimethylamino)phosphonium hexafluorophosphate (BOP), (1-cyano-2-ethoxy-2-oxoethylidenaminooxy)-dimethylamino-morpholino-carbenium hexafluorophosphate (COMU) and O-[(ethoxycarbonyl)-cyanomethyleneamino]-N,N,N',N'-tetramethyluronium tetrafluoroborate (TOTU).

The carboxylic acid of the tetrahydroisoquinoline may require protection during amidation of the tetrahydroisoquinoline nitrogen atom. Suitable protecting groups are known and can be found in Greene & Wutz, Protective Groups in Organic Synthesis, 3$^{rd}$ Edition, John Wiley & Sons.

In some cases, the carboxylic acid used to introduce $R_1$ may be activated in the form of a cyclic active amide. Use of a cyclic active amide of 2,2-diphenylethanoic acid reduces the need for this temporary protection of the isoquinoline carboxylic acid as the cyclic active amide is more selective for reaction with the isoquinoline nitrogen. The cyclic active amide may be formed by reaction of the 2,2-diphenyl ethanoic acid chloride with a 5 membered nitrogen containing heterocycle. Examples of suitable heterocycles include pyrazole, pyrrole, imidazole, 1,2,3-triazole and 1,2,4-triazole.

The carboxylic acid at $R_2$ or $R_3$ may be modified to provide a carboxylic acid bioisostere or other group such as an alcohol, amide or nitrile. Conversion of a carboxylic acid to alcohol by reduction, amide by amidation and nitrile by heating with a halonitrile are methods well known in the art.

The carboxylic acid may also be readily converted to a sulfonamide by reaction with an appropriate sulfonamide or sulfonyl urea. An example is shown in Scheme 4:

Scheme 4

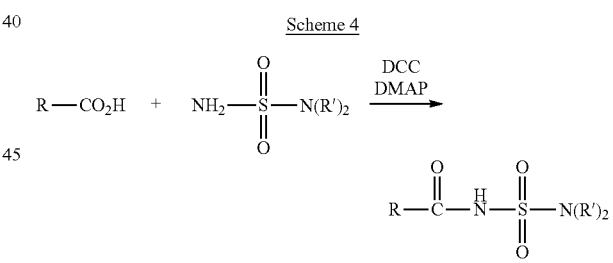

where R is the tetrahydroisoqunoline and each R' is independently a group such as hydrogen, alkyl, alkenyl, alkynyl, aryl, cycloalkyl, heteroaryl or heterocyclyl.

Tetrazole carboxylic acid bioisosteres may be prepared by the treatment of a nitrile with an azide in the presence of iodine as shown in scheme 5:

Scheme 5

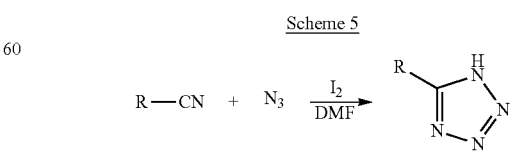

During any synthetic procedure, reactive functional groups may require protecting to avoid unwanted reaction and to ensure reaction at a specified site. Suitable protecting groups are known in the art and may be found in Greene & Wutz, ibid.

METHODS OF THE INVENTION

In one aspect of the present invention, there is provided a method of treating or preventing the symptoms of a neuropathic condition in a subject comprising administering a compound of formula (I) or a pharmaceutically acceptable salt thereof.

The compounds of formula (I) are effective in the prevention or attenuation of the symptoms of neuropathic conditions including primary and secondary neuropathic conditions. In accordance with the present invention, the compounds of formula (I) can act to treat, prevent or attenuate one or more symptoms associated with neuropathic conditions including, but not limited to, neuropathic pain, hyperesthesia, hyperalgesia, allodynia and/or spontaneous burning pain. In some embodiments, the compound of formula (I) is used to prevent or attenuate one or more symptoms associated with peripheral neuropathic conditions, illustrative examples of which include numbness, weakness, burning pain, shooting pain, and loss of reflexes. The pain may be severe and disabling. In some embodiments, the symptom, which is the subject of the prevention and/or attenuation, is neuropathic pain. Accordingly, in a related aspect, the invention provides methods for preventing and/or attenuating neuropathic pain in an individual, comprising administering to the individual a pain-preventing or -attenuating effective amount of an $AT_2$ receptor antagonist, which is suitably in the form of a pharmaceutical composition.

There are many possible causes of neuropathy and neuropathic pain and it will be understood that the present invention contemplates the treatment or prevention of symptoms of any neuropathic condition regardless of the cause. In some embodiments, the neuropathic conditions are a result of diseases of the nerves (primary neuropathy) and neuropathy that is caused by systemic disease (secondary neuropathy) such as but not limited to: diabetic neuropathy; Herpes Zoster (shingles)-related neuropathy; uremia-associated neuropathy; amyloidosis neuropathy; HIV sensory neuropathies; hereditary motor and sensory neuropathies (HMSN); hereditary sensory neuropathies (HSNs); hereditary sensory and autonomic neuropathies; hereditary neuropathies with ulcero-mutilation; nitrofurantoin neuropathy; tomaculous neuropathy; neuropathy caused by nutritional deficiency, neuropathy caused by kidney failure and complex regional pain syndrome. Other causes include repetitive activities such as typing or working on an assembly line, medications known to cause peripheral neuropathy such as several antiretroviral drugs (ddC (zalcitabine) and ddI (didanosine), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillian-Barre syndrome). In certain embodiments, the neuropathic condition is a peripheral neuropathic condition, which is suitably pain secondary to mechanical nerve injury or painful diabetic neuropathy (PDN) or related condition.

The neuropathic condition may be acute or chronic and, in this connection, it will be understood by persons of skill in the art that the time course of a neuropathy will vary, based on its underlying cause. With trauma, the onset of symptoms may be acute, or sudden; however, the most severe symptoms may develop over time and persist for years. Inflammatory and some metabolic neuropathies have a subacute course extending over days to weeks. A chronic course over weeks to months usually indicates a toxic or metabolic neuropathy. A chronic, slowly progressive neuropathy over many years such as occurs with painful diabetic neuropathy or with most hereditary neuropathies or with a condition termed chronic inflammatory demyelinating polyradiculoneuropathy (CIDP). Neuropathic conditions with symptoms that relapse and remit include the Guillian-Barré syndrome.

In another aspect of the invention there is provided a method of treating or preventing a condition characterized by neuronal hypersensitivity in a subject comprising administering a compound of formula (I) or a pharmaceutically acceptable salt thereof.

In some embodiments, the condition characterized by neuronal hypersensitivity is a hyperalgesic condition such as fibromyalgia. In other embodiments, the condition is irritable bowel syndrome which is characterized by neuronal hypersensitivity in the gut.

In another aspect of the invention there is provided a method of treating or preventing a disorder associated with aberrant nerve regeneration comprising administering a compound of formula (I) or a pharmaceutically acceptable salt thereof.

In some embodiments, the disorder associated with aberrant nerve regeneration also includes neuronal hypersensitivity. Examples of disorders associated with aberrant nerve regeneration are breast pain, interstitial cystitis and vulvodynia. In other embodiments, the disorder is a cancer chemotherapy-induced neuropathy.

In another aspect of the invention, there is provided a method of treating or preventing inflammatory pain in a subject comprising administering a compound of formula (I) or a pharmaceutically acceptable salt thereof.

Pain related to inflammation may be acute or chronic and can be due to a number of conditions that are characterized by inflammation including, without limitation, burns such as chemical, frictional or chemical burns, autoimmune diseases such as rheumatoid arthritis and osteoarthritis, inflammatory bowel disease such as Crohn's disease and colitis, and other inflammatory diseases such as inflammatory bowel disease, carditis, dermatitis, myositis, neuritis and collagen vascular diseases.

In a further aspect, the present invention provides a method of treating or preventing impaired nerve conduction velocity in a subject comprising administering a compound of formula (I) or a pharmaceutically acceptable salt thereof.

Impaired nerve conduction velocity is a symptom of nerve dysfunction or damage and may be present as a symptom of a large number of diseases or disorders, particularly diseases or disorders that exhibit paresthesia as a symptom. In some embodiments, the impaired nerve conduction velocity is associated with a neuropathic condition as described above. In other embodiments, the impaired nerve conduction velocity is associated with Carpel Tunnel Syndrome, ulnar neuropathy. Guillian-Barré Syndrome, fascioscapulohumeral muscular dystrophy and spinal disc herneation. In some embodiments, the symptoms of impaired nerve conduction velocity are non-painful symptoms.

Nerve conduction velocity is assessed by evaluating the electrical conduction of motor and sensory nerves in the body. Motor nerve conduction velocity is measured by stimulation of a peripheral nerve and measuring the time taken for the electrical impulse to be detected in the muscle associated with the nerve. The time taken is measured in milliseconds and is converted to a velocity (m/s) by taking into account the distance traveled. Sensory nerve conduction is assessed in a similar manner with stimulation of a peripheral nerve and recording at a sensory site such as a finger or paw pad.

In yet a further aspect of the invention there is provided a method of producing analgesia in a subject comprising administering a compound of formula (I) or a pharmaceutically acceptable salt thereof.

In some embodiments, the subject is a subject having a neuropathic condition, an inflammatory condition, impaired nerve conduction velocity, a condition characterized by neuronal hypersensitivity or a disorder associated with aberrant nerve regeneration. In other embodiments, the subject is a subject at risk of developing neuropathic pain, inflammatory pain, pain related to impaired nerve conduction velocity, a condition characterized by neuronal hypersensitivity or a disorder associated with aberrant nerve regeneration.

In still another aspect of the invention there is provided a method of treating or preventing a cell proliferative disorder in a subject comprising administering a compound of formula (I) or a pharmaceutically acceptable salt thereof.

In some embodiments, the cell proliferative disorder is a cancer, especially where the cancer is selected from leukaemia, melanoma, prostate cancer, breast cancer, ovarian cancer, basal cell carcinoma, squamous cell carcinoma, sarquoides, fibrosarcoma, colon cancer, lung cancer and other solid tumour cancers.

In other embodiments, the cell proliferative disorder is a non-cancerous proliferative disorder. Examples of such non-cancerous proliferative disorders include dermatological disorders such as warts, keloids, psoriasis, proud flesh disorder and also the reduction in scar tissue and cosmetic remodelling.

In a further aspect the present invention provides a method of treating or preventing a disorder associated with an imbalance between bone resorption and bone formation in a subject comprising administering a compound of formula (I) or a pharmaceutically acceptable salt thereof.

In some embodiments, the disorder associated with an imbalance between bone resorption and bone formation is osteoporosis.

The subjects, individuals or patients to be treated are mammalian subjects including but not limited to humans, primates, livestock animals such as sheep, cattle, pigs, horses, donkeys and goats; laboratory test animals such as mice, rats, rabbits and guinea pigs; companion animals such as cats and dogs or captive wild animals such as those kept in zoos. In a particular embodiment, the subject is a human.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prevention" is to be considered in its broadest context. The term "treatment" does not necessarily imply that a subject is treated until total recovery. "Treatment" may also reduce the severity of an existing condition. The term "prevention" does not necessarily mean that the subject will not eventually contract a disease condition. The term "prevention" may be considered to include delaying the onset of a particular condition. Accordingly, treatment and prevention include amelioration of the symptoms of a particular condition or preventing or otherwise reducing the risk of developing a particular condition.

In some embodiments, the compounds of formula (I) or their pharmaceutically acceptable salts thereof may be administered together with another therapy. Administration may be in a single composition or in separate compositions simultaneously or sequentially such that both compounds or therapies are active at the same time in the body.

In some embodiments, the compounds of formula (I) or their pharmaceutically acceptable salts are administered together with another therapy to treat neuropathic or inflammatory pain or the underlying condition that is causing the neuropathic or inflammatory pain or another therapy to treat conditions characterized by neuronal hypersensitivity, disorders associated with aberrant nerve regeneration, proliferative disorders or disorders associated with an imbalance between bone resorption and bone formation. In some embodiments, the amount of the second drug may be reduced when administration is together with a compound of formula (I) or a pharmaceutically acceptable salt thereof.

Suitable additional drugs to treat pain include opiates such as morphine, codeine, dihydrocodeine, hydrocodone, acetyldihydrocodeine, oxycodone, oxymorphone and buprenorphine, and non-steroidal anti-inflammatory drugs (NSAIDs) such as aspirin, ibuprofen, naproxen, acetaminophen, diflunisal, salsalate, phenacetin, fenoprofen, ketoprofen, flurbiprofen, oxaprozin, loxoprofen, indomethacin, sulindac, etodolac, ketorolac, diclofenac, nabumetone, mefenamic acid, meclofenamic acid, flufenamic acid, tolfenamic acid, celecoxib, parecoxib, lumaricoxib, etoricoxib, firocoxib, rimesulide and licofelone.

Examples of drugs to treat neuropathies include duloxetine, pregabalin, gabapentin, phenytoin, carbamazebine, levocarnitine, tricyclic antidepressants such as amitryptiline and sodium channel blockers such as lidocaine.

Examples of chemotherapy drugs for proliferative disorders include cisplatin, carboplatin, camptothecin, carmustine, cyclophosphamide, dactinomycin, daunorubicin, dexamethasone, docetaxel, doxorubicin, etoposide, epirubicin, everolimus, gemcitibine, goserelin, trastuzumab (Herceptin®), idarubicin, interferon-alfa, irinotecan, methotrexate, mitomycin, oxaliplatin, paclitaxel, raloxifene, streptozocin, tamoxifen, topotecan, vinblastine, vincristine, abiraterone, fluorouracil, denosumab, imatinib, geftinib, lapatinib, pazopanib, rituximab, sunitinib, erlotinib and vorinistat.

Examples of drugs to treat disorders associated with an imbalance between bone formation and bone resorption include bisphosphonates such as sodium alendronate, risedronate and ibandronate, raloxifene, calcitonin, teriparatide, strontium ranelate or calcium supplements.

Examples of drugs used to treat conditions characterized by neuronal hypersensitivity, such as irritable bowel syndrome, include $5HT_3$ receptor antagonists such as alosetron (Lotronex®).

The $AT_2$ receptor antagonists of the invention are also useful in combination with radiotherapy in cancer patients.

COMPOSITIONS OF THE INVENTION

While it is possible that, for use in therapy, a compound of the invention may be administered as a neat chemical, it is preferable to present the active ingredient as a pharmaceutical composition.

Thus, in a further aspect of the invention, there is provided a pharmaceutical composition comprising a compound of formula (I) or a pharmaceutically acceptable salt thereof and at least one pharmaceutically acceptable carrier.

The carrier(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcelluose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compositions of the invention may comprise further active ingredients such as therapies for treating neuropathic or inflammatory pain or the underlying condition causing the neuropathic or inflammatory pain or therapies for treating impaired nerve conduction velocity, conditions characterized by neuronal hypersensitivity, disorders associated with aberrant nerve regeneration, proliferation disorders or disorder associated with an imbalance between bone resorption and bone formation.

The invention will now be described with reference to the following Examples which illustrate some preferred aspects of the present invention. However, it is to be understood that the particularity of the following description of the invention is not to supersede the generality of the preceding description of the invention.

EXAMPLES

Abbreviations:

| | |
|---|---|
| DCM | dichloromethane |
| DBU | 1,8-diazabicyclo[5,4-0]undec-7-ene |
| RT | room temperature |
| PE | petroleum ether |
| EA or EtOAc | ethyl acetate |
| THF | tetrahydrofuran |
| LiOH | lithium hydroxide |
| MeOH | methanol |
| DMAP | 4-dimethylaminopyridine |
| TBTU | O-(benzotriazol-1-yl)-N,N,N',N'-tetramethyluronium tetrafluoroborate |
| Bn | benzyl |
| Bz | benzoyl |
| TLC | thin layer chromatography |
| DCC | N,N'-dicylohexylcarbodiimide |
| DMF | dimethylformamide |
| EDTA | ethylene diamine tetraacetic acid |
| PBS | phosphate buffered saline |
| EtOH | ethanol |
| Boc | t-butyloxycarbonyl |
| DMSO | dimethylsulfoxide |

General Methods Used in the Synthesis Examples

LC-MS (Agilent):
1. LC: Agilent Technologies 1200 series, Binary Pump. Diode Array Detector. Ultimate AQ-C18, 3 µm, 2.1×50 mm column. Mobile phase: B (MeOH) and A (0.07% HCOOH aqueous solution). Flow Rate: 0.4 ml/min at 25° C. Detector: 214 nm, 254 nm. Gradient stop time, 5 min. Timetable:

| T (min) | B(%) | A(%) |
|---|---|---|
| 0 | 10 | 90 |
| 0.2 | 10 | 90 |
| 1.2 | 95 | 5 |
| 2.8 | 95 | 5 |
| 3 | 10 | 90 |
| 5 | 10 | 90 |

2. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C. Vcap: 3500V.
3. Sample preparation: samples were dissolved in methanol at 1~10 µg/mL, then filtered through a 0.22 µm filter membrane. Injection volume: 1~10 µL.

LC-MS (Agilent, P-2) (Positive Ion mode) or LC-MS (Agilent, N-2) (Negative Ion Mode):
1. LC: Agilent Technologies 1200 series, Binary Pump, Diode Array Detector. Xbridge-C18, 2.5 µm, 2.1×30 mm column. Mobile phase: B (MeOH) and A (0.07%

HCOOH aqueous solution). Flow Rate: 0.5 mL/min at 30° C. Detector 214 nm, 254 nm. Gradient stop time, 5 min. Timetable:

| T (min) | B(%) | A(%) |
|---|---|---|
| 0 | 80 | 20 |
| 0.2 | 80 | 20 |
| 0.8 | 5 | 95 |
| 2.8 | 5 | 95 |
| 3 | 80 | 20 |
| 5 | 80 | 20 |

2. MS: G6110A, Quadrupole LC/MS, Ion Source: ES-API, TIC: 50~900 m/z. Fragmentor: 60, Drying gas flow: 10 L/min, Nebulizer pressure: 35 psi, Drying gas temperature: 350° C., Vcap: 3500V.
1. Sample preparation: samples were dissolved in methanol at 1~10 µg/mL, then filtered through a 0.22 µm filter membrane. Injection volume: 1~10 µL.

Analytical HPLC:
1. (Referred to as "Aligent") Agilent Technologies 1200 series, Quaternary Pump, Diode Array Detector. Ultimate AQ-C18, 5 µm, 4.6×250 mm column. Mobile Phase: B (MeOH) and A (0.07% TFA aqueous solution). Flow Rate: 1.00 mL/min at 30° C. Detector 214 nm, 254 nm. Gradient stop time: 20 min. Timetable:

| T (min) | B(%) | A(%) |
|---|---|---|
| 0 | 40 | 60 |
| 3 | 40 | 60 |
| 5 | 60 | 40 |
| 7 | 80 | 20 |
| 8 | 95 | 5 |
| 15 | 95 | 5 |
| 17 | 40 | 60 |
| 20 | 40 | 60 |

2. Sample preparation: samples were dissolved in methanol at ~1 mg/mL, then filtered through a 0.22 µm filter membrane. Injection volume: 1~10 µL.

Referred to as "JULY-L"
1. Agilent Technologies 1200 series, Quaternary Pump, Diode Array Detector. Waters Nova-pak C18, 4 µm, 3.9×150 mm column. Mobile Phase: C (MeOH) and D (0.07% TFA aqueous solution). Flow Rate: 1.00 mL/min at 30° C. Detector: 214 nm, 254 nm. Gradient stop time: 15 min. Timetables:

Method Name: JULY-L (Average an Low Polarity)

| T (min) | C(%) | D(%) |
|---|---|---|
| 0 | 20 | 80 |
| 2 | 20 | 80 |
| 4 | 40 | 60 |
| 5 | 70 | 30 |
| 6 | 95 | 5 |
| 10 | 95 | 5 |
| 11 | 70 | 20 |
| 12 | 20 | 80 |
| 15 | 20 | 80 |

2. Sample preparation: samples were dissolved in methanol at ~1 mg/mL, then filtered through a 0.22 µm filter membrane. Injection volume: 1~10 µL.

Example 1: Preparation of Compound 33

1. Procedure for the Preparation of Compound 33b

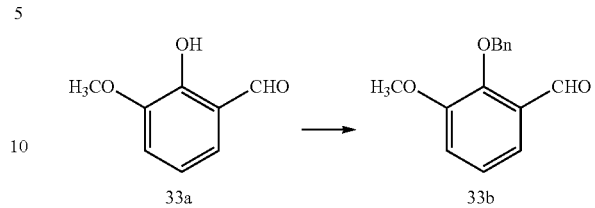

To a solution of compound 33a (39.95 kg, 262 Mol) and potassium carbonate (39.9 kg, 288 Mol) in 300 kg acetone, benzyl bromide (47.2 kg, 276 Mol) was added at a temperature between 10 and 15° C. The mixture was heated to reflux at 60° C. during 1.5-2.5 hours and the conversion was monitored by TLC. After consumption of compound 33a, water (53 L) and toluene (115 kg) were added to the mixture. The organic phase was washed two times with brine (2×59 L) and evaporated under reduced pressure. Isopropyl ether (232 kg) was added to the residual solid at 40° C. and when dissolution was complete, 427 kg hexane was added and the solution was cooled to 2° C. The solid was filtered off, washed with hexane and dried at 35° C. for 56 hours to give 35.7 kg of compound 33b. Re-extraction of the mother liquor gave another 7.75 kg of compound 33b which was analytically identical to the initial extraction. The combined yield of 43.45 kg (68.3%) was obtained.

2. Procedure for the Preparation of Compound 33d

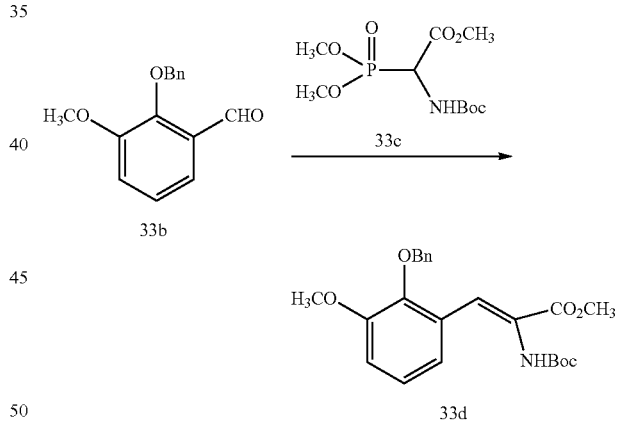

To a stirred solution of phosphonate 33c (61.3 kg, 206 Mol) and tetramethylguanidine (24.8 kg, 215 Mol) in 100 kg of THF, a solution of compound 33b (43.45 kg, 179 Mol) in 100 kg of THF was added at a temperature between 0 to 5° C. over a period of 100 minutes. After the complete addition of reactants. TLC showed complete consumption of compound 33b. The THF was removed under reduced pressure and ethyl acetate (129 kg) was added to the remaining oily mixture. The ethyl acetate phase was washed with 10% citric acid (143 L) and with 10% brine (4×39 L). The purification was performed using silica column chromatography with 140 kg silica. The product was eluted with ethyl acetate: hexane (1:4 w/w). The solvents were evaporated under reduced pressure to yield about 70 kg (94.4%) of compound 33d. TLC showed a purity of >99%.

3. Procedure for the Preparation of Compound 33e

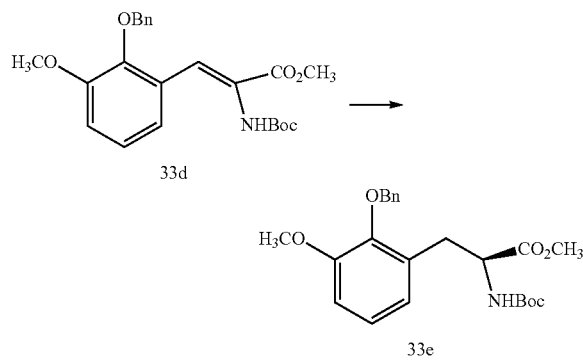

A 250 L pressure vessel was charged with a solution containing 150 kg of toluene and about 15 kg (36.2 Mol) of compound 33d. The solution was degassed with nitrogen 3 times at 5 bar, and was cooled to 15° C. During this time a catalyst solution was prepared by combining the BoPhoz ligand (150 g, 245 mmol, 1.07 eq) and bis(1,5-cyclooctadiene)rhodium (I) tetrafluoroborate (92.6 g, 228 mmol, 1.00 equiv.) in 5.0 L of THF under a constant flow of nitrogen. After complete formation of the complex, a deep red solution was obtained, the preformed catalyst was added to the solution of compound 33d.

The 250 L vessel was then pressurized twice with nitrogen and 3 times with hydrogen and the temperature of the vessel was maintained at 15° C. The reaction was followed by controlling the hydrogen uptake using a mass flow meter. The reaction was stirred under hydrogen pressure of 2 bar for a total of 12 h. Chiral HPLC analysis of the reaction mixture indicated >99.9% conversion to compound 33e with over 99.5% ee.

The solution was treated with charcoal (0.76 kg) and filtered through silica (10 kg). The solvent was distilled off under pressure and the resulting oil was dissolved with isopropyl ether (234 kg) and filtered through 1.2 μm filter to remove any traces of BoPhoz/BoPhoz-oxide. The solution was evaporated under reduced pressure to give compound 33e.

4. Procedure for the Preparation of Compound 33f

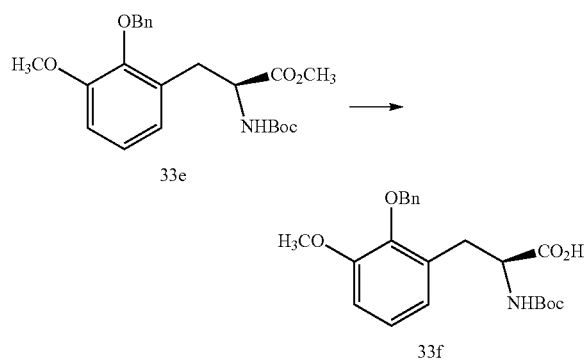

To a solution of lithium hydroxide (12.2 kg, 290 Mol) in 314 L water was added a solution of compound 33e (60.3 kg, 145 Mol) in THF (200 L) at 17° C. The reaction was stirred for one hour and TLC analysis indication >99% conversion to compound 33f. After neutralization with citric acid to a pH of 5, the THF was evaporated under reduced pressure at 33° C., and the mixture was dissolved with ethyl acetate (272 kg), washed with a 10% citric acid solution (160 L), and a 10% brine solution (4×, total 118 L) to reach a pH of 5. The ethyl acetate phase was evaporated under reduced pressure to a final volume of 100 L, 215 kg ethyl acetate was added and distilled off again to reduce water content to about 0.04%. TLC showed compound 33f was obtained in over 99% purity.

5. Procedure for the Preparation of Compound 33g

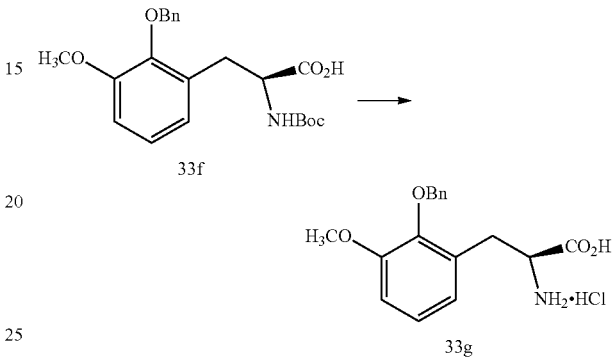

A solution of compound 33f (55.3 kg) in 320 L ethyl acetate was combined with 3.9 M HCl in ethyl acetate (241 kg) at 10° C. After 2 hours TLC analysis showed >99% conversion to compound 33g. Isopropyl ether (160 kg) was added and after stirring for one hour at 10° C. the reaction mixture was filtered and washed with isopropyl ether (2×46 L). A wet solid (123 kg) was obtained and dried in a vacuum cone-dryer with nitrogen purge at 35° C. for about 60 hours. Compound 33g (50.45 kg, 83.3%) was obtained as a white powder.

6. Procedure for the Preparation of Compound 33h

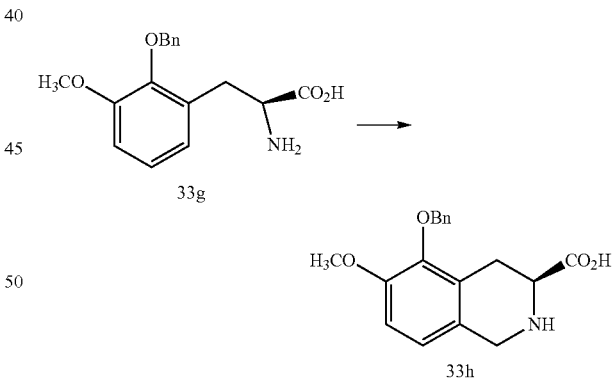

To a stirred solution of compound 33g (60.0 g, 195 mmol) in 990 mL water, was added a solution of $Na_2CO_3$ (10.7 g, 101 mmol) in 60 mL water to reach a pH of 5. The white suspension was diluted with 300 mL of water, the mixture was filtered and the white solid washed with 200 mL water. The wet product was suspended in 540 mL water, with phosphoric acid (85%, 21 mL) and aqueous formaldehyde (37%, 22 mL). The white reaction mixture was heated to 60° C. At 50° C., the mixture became homogeneous and after a further 30 minutes at 60° C., a while precipitate formed. The suspension was heated for 12 hours and the reaction monitored by TLC. After complete conversion, the suspension was cooled to 22° C. and a solution of sodium acetate (24.5 g) in water (74 mL) was added to reach a pH of 3. After filtration and washing with water (3×150 mL) and with acetone (100 mL), the white solid was dried at 30° C. under reduced pressure to give compound 33h as a white homogeneous powder (43.4 g, 71%).

7. Procedure for the Preparation of Compound 33i

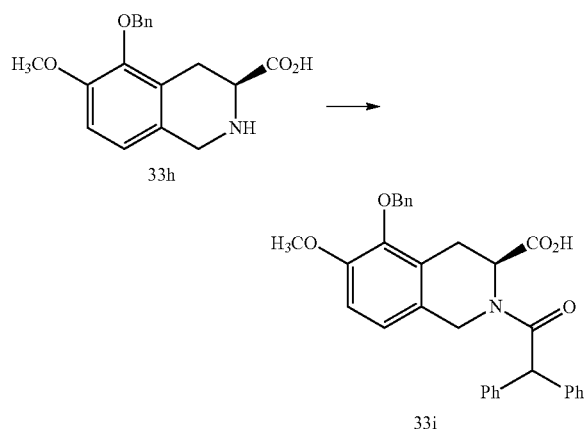

Pyrazole Active Ester Formation

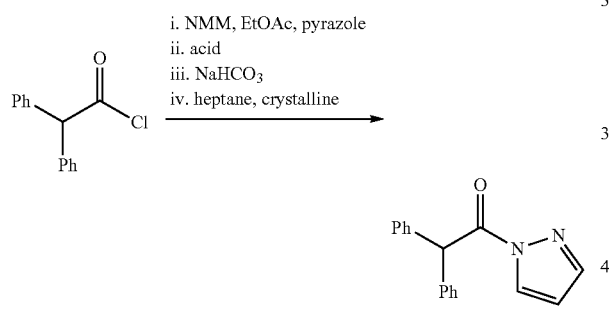

A glass or stainless steel jacketed vessel was placed under an inert atmosphere. To the vessel were charged pyrazole (1.1eq). N-methylmorpholine (NMM) (1.3eq) and ethyl acetate. An ethyl acetate solution of diphenylacetyl chloride (1.0eq) was added gradually. Cooling of the reaction vessel was applied so as to maintain an internal temperature below +30° C. Following complete addition the contents were stirred for a minimum of 20 minutes. The reaction mixture was washed with water, 1M sulphuric acid (2×), saturated aqueous sodium bicarbonate (2×), water and brine. The ethyl acetate phase was concentrated and the residue was stripped with heptane.

The residue was heated to 70° C. in heptane so as to dissolve all solids. The resulting solution was cooled and held at 15±5° C. for 1 h with concomitant crystallization. The crystals were filtered and dried for a minimum of 16 h. Yield: 80-90% from diphenylacetyl chloride.

Isoquinoline Acylation

A glass lined or stainless steel vessel was placed under an inert atmosphere. To the vessel was charged DMF, tetramethylguanidine (1.03eq) and compound 33h (1.0eq). The mixture was stirred for approximately 1 h to allow dissolution to occur (only partial dissolution was expected at this stage). To the reaction mixture was charged pyrazole active ester (1.2eq). The reaction mixture was stirred for a minimum of 16 h. An IPC (HPLC) was performed to verify the extent of reaction. Dimethylethylenediamine (0.3eq) was charged to the reaction mixture and stirring continued for a further 2 h.

The reaction mixture was diluted with toluene and washed with 1M sulfuric acid (2×) and water (2×). The organic phase was reduced in volume through evaporation of solvent. Sodium ethoxide (1.0eq) was charged to the reaction mixture. The remaining solvent was evaporated from the reaction mixture. The residue was evaporated from ethyl acetate.

The crude product was agitated in ethyl acetate and the mixture transferred to a stirred vessel. Iso-propanol was charged to the ethyl acetate solution in a controlled addition causing crystallization to occur. The mixture was stirred for a minimum of 1 h. The crystals were filtered and washed with a small volume of iso-propanol. The crystals were dried under vacuum for a minimum of 16 h giving Compound 33i.

8. Procedure for the Preparation of Compound 33j

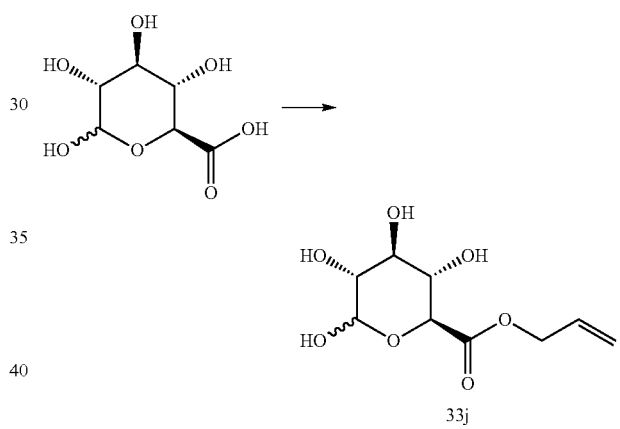

A solution of D-glucuronic acid (2.0 g, 10.3 mmol) in DMF (20 mL) was treated with DBU (1.69 mL, 11.33 mmol) and then allyl bromide (1.07 mL, 12.4 mmol). The resulting mixture was stirred at ambient temperature for 16 hours. The solvent was evaporated and the residue diluted with acetone (40 mL), causing an oily residue to deposit. The supernatant was applied to a silica column and eluted with 25% toluene in acetone giving an oil. The oil was crystallized from acetone/toluene and the resulting white crystals dried to give 1.026 g (43%) of compound 33j.

9. Procedure for the Preparation of Compound 33k

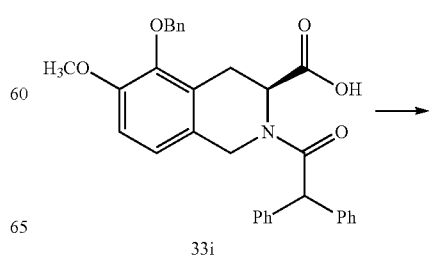

-continued

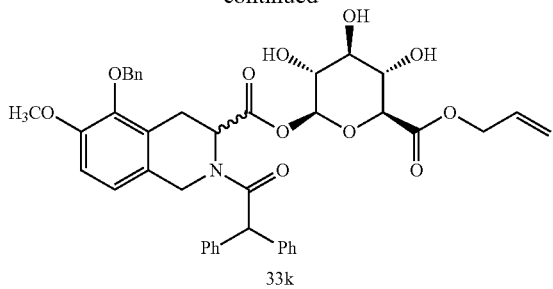

33k

Compound 33i (1.71 g, 3.02 mmol, 90% purity as estimated by $^1$H NMR) and glucuronic acid allyl ester compound 33j (1.026 g, 3.02 mmol, 69% purity as estimated by $^1$H NMR) were evaporated from acetonitrile (2×30 mL) to remove residual water present. The residue was dissolved in acetonitrile (30 mL) and treated with NMM (0.67 mL), 6.05 mmol) and then TBTU (971 mg, 3.02 mmol). The resulting mixture was stirred at ambient temperature for 16 hours. The reaction mixture was treated with approximately 3 g of Amberjet™ strongly acidic resin. The resin was filtered off and the filtrates evaporated. The residue was purified by flash silica chromatography, eluting with 3% increasing to 5% ethanol in dichloromethane. Evaporation of the product containing fractions gave 1.671 g (76%) orange oil. HPLC analysis indicated the desired diasteromeric product mixture compound 33k in good purity.

10. Procedure for the Preparation of Compound 33

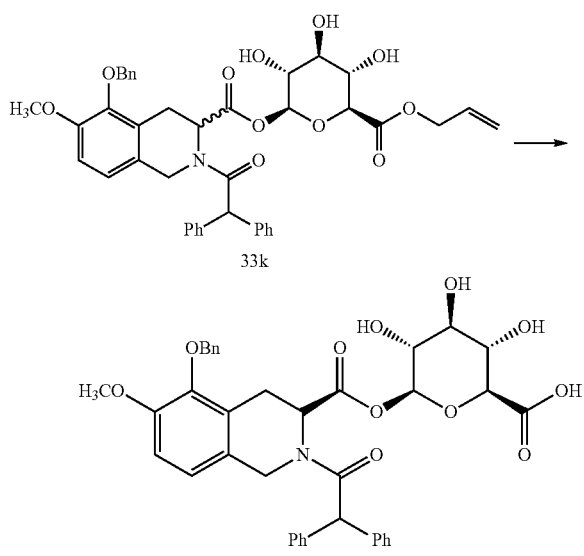

Compound 33k (1.661 g, 2.30 mmol) and N,N'dimethyl-barbitutic acid (358 mg, 2.30 mmol) were dissolved in THF (20 mL) and degassed. Palladium tetrakis(triphenylphosphine) (27 mg, 0.023 mmol) was added and the mixture stirred at ambient temperature under argon. After 2 hours the reaction mixture was evaporated on to silica (8 g) and the residue purified by flash silica chromatography, eluting with first 5% ethanol in dichloromethane and them 20:79:1 [ethanol:DCM:acetic acid] to elute the product. Evaporation of solvent gave an orange oil which crystallized on standing, the material was stirred in 1:1 methanol:water (30 mL) for 1 hour. The resulting mixture was filtered and the solid dried to give 42 mg compound 33 as a white powder.

Example 2: Preparation of Compound 34

2. Procedure for the Preparation of Compound 34b

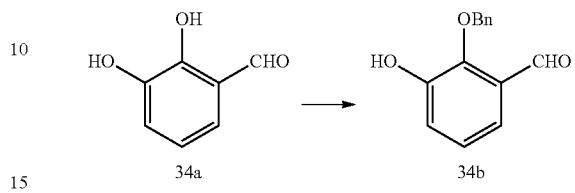

Dihydroxybenzaldehyde, compound 34a (1 g, 7.24 mmol) was stirred in THF (15 mL) and NaH added (290 mg, 7.24 mmol) forming a thick yellow precipitate. After 20 minutes the mixture was cooled to 0° C. and benzyl bromide (0.87 mL, 7.23 mmol) was added dropwise. The mixture was allowed to warm to ambient temperature; a thick yellow slurry remained. The mixture was diluted with DMF (10 mL). After stirring for 16 hours, TLC suggested only partial reaction.

The solvent was evaporated and the residue dissolved in DMF (10 mL) and treated with further benzyl bromide (0.87 mL, 7.24 mmol). Within 10 minutes, the solution had begun to decolorise and become homogenous. After 4 hours the solution was diluted with toluene and washed with water (3×), dried (MgSO$_4$) and evaporated. The residue was purified by flash silica chromatography, eluting with 8:1 then 6:1 EA:PE (60/80). The product containing fractions were evaporated to give compound 34b (1.031 g, 62%) as a white solid.

2. Procedure for the Preparation of Compound 34d

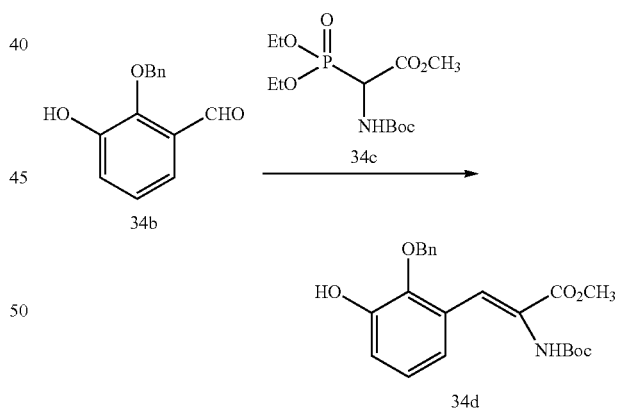

To a stirred solution of phosphonate 34c (1.611 g, 5.42 mmol) and aldehyde 34b (1.031 g, 4.52 mmol) in THF (10 mL) was added tetramethylguanidine (1.25 mL, 9.94 mmol). The reaction mixture was stirred at ambient temperature for 16 hours. The reaction mixture was diluted with water and the THF evaporated. The residue was acidified using 1M aqueous hydrochloric acid and extracted with ethyl acetate. The organic extract was dried (MgSO$_4$) and evaporated to give a brown oil. The residue was purified by flash silica chromatography, eluting with 4:1 then 3:1 PE (60/80):EA affording compound 34d as a white solid (1.59 g, 88%).

3. Procedure for the Preparation of Compound 34e

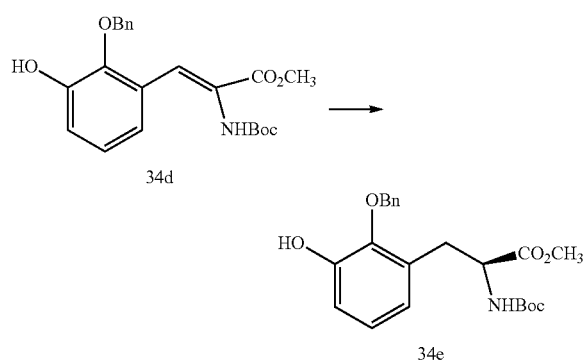

34d

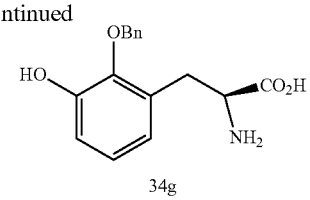

34g

Compound 34f (0.73 g, 1.88 mmol) was stirred in 1,4-dioxane (10 mL) and treated with hydrogen chloride gas (approximately 0.04 mol). The resulting solution was stirred at ambient temperature for 1 hour. Additional hydrogen chloride gas (approximately 0.04 mol) was bubbled through the solution. The residue was dried under high vacuum to give compound 34g as a colourless oil (608 mg, 100%).

6. Procedure for the Preparation of Compound 34h

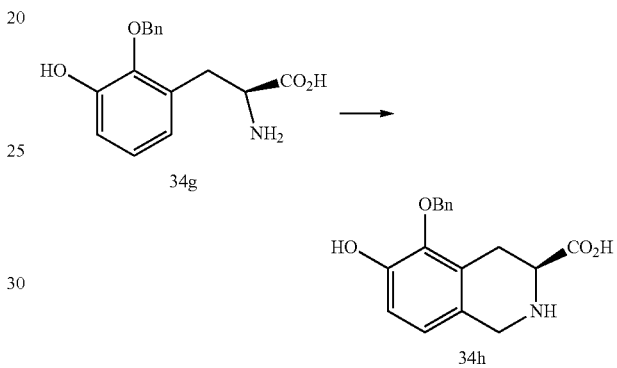

A solution of compound 34d (1.59 g, 3.97 mmol) and rhodium[(S,S)-diEtDuPhos][COD]OTf (57 mg, 0.079 mmol) in methanol (90 mL) was degassed. The resulting solution was stirred under a balloon pressure of hydrogen for 2 hours. $^1$H NMR analysis of the reaction mixture indicated no reaction had occurred.

The reaction mixture was charged to a high pressure reaction vessel and degassed. Further catalyst (57 mg, 0.079 mmol) was added and the solution degassed and stirred under 5 bar hydrogen pressure for 3 hours. The reaction mixture was evaporated and the residue purified by flash chromatography, eluting with 25% EA in PE (60/80), giving compound 34e as a colourless oil (1.46 g, 91%).

4. Procedure for the Preparation of Compound 34f

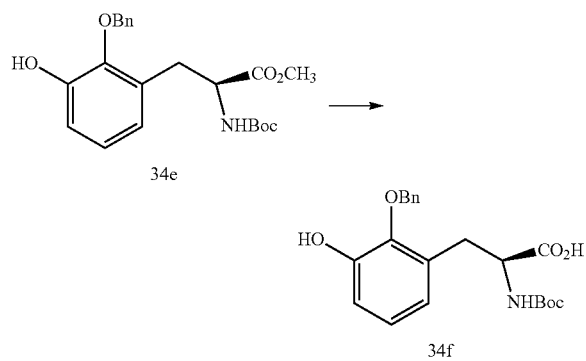

Compound 34e (1.46 g, 3.63 mmol) was stirred in THF (15 mL) and lithium hydroxide monohydrate (380 mg, 9.07 mmol) was added in a single portion. Stirring was continued for 1 hour. Further lithium hydroxide monohydrate (76 mg, 1.81 mmol) was added and stirring continued for 30 minutes. The mixture was acidified with 1M aqueous hydrochloric acid and extracted with ethyl acetate (2×), dried with MgSO$_4$ and evaporated to give compound 34f as a colourless oil (1.44 g, 102%).

5. Procedure for the Preparation of Compound 34g

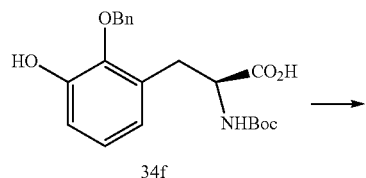

34f

To a solution of compound 34g (608 mg, 1.88 mmol) in 1M aqueous hydrochloric acid (10 mL) was added aqueous formaldehyde (0.84 mL, 11.3 mmol, 37% w/w). The resulting solution was heated at 60° C. for 1 hour and treated with a solution of sodium acetate (1.23 g, 15 mmol) in water (5 mL). The mixture was held at 4° C. for 2 hours, causing formation of a white solid. The solid was filtered and dried by co-evaporation with ethanol to give compound 34h as a white solid (330 mg, 59%).

7. Procedure for the Preparation of Compound 34

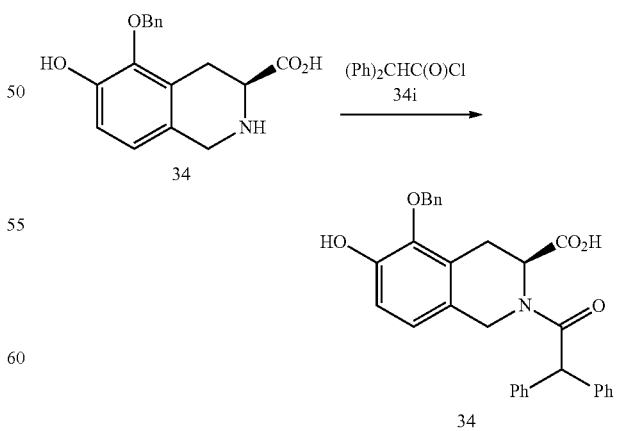

A suspension of compound 34h (313 mg, 1.05 mmol) in DCM (10 mL) at 0° C. was treated with pyridine (0.59 mL, 7.32 mmol) and chlorotrimethyl silane (0.66 g, 5.23 mmol).

After 5 minutes acid chloride 34i (224 mg, 0.97 mmol) was added in a single portion. The reaction mixture was warmed to ambient temperature, diluted with ethyl acetate and extracted with 1M aqueous hydrochloric acid (2×), dried (MgSO$_4$) and evaporated. The residue was purified by flash silica chromatography, eluting with 50% EA in PE (+1% acetic acid) affording a colourless oil. $^1$H NMR and MS analysis indicated that the 6-phenol had not been fully desilylated.

The oil was dissolved in THF (10 mL) and treated with tetrabutylammonium fluoride (0.84 mL, 1.0 M in THF). After 2 hours the reaction mixture was diluted with ethyl acetate, washed with 1M aqueous hydrochloric acid, dried (MgSO$_4$) and evaporated. The residue was purified by flash silica chromatography, eluting with 2:1 then 1:1 PE (60/80): EA (+0.5% acetic acid). The product containing fractions were evaporated to give a colourless oil. The oil was evaporated from EA (3×) and dried to give compound 34 as a yellow foam (4.14 mg, 80%).

Example 3: Preparation of Compound 40

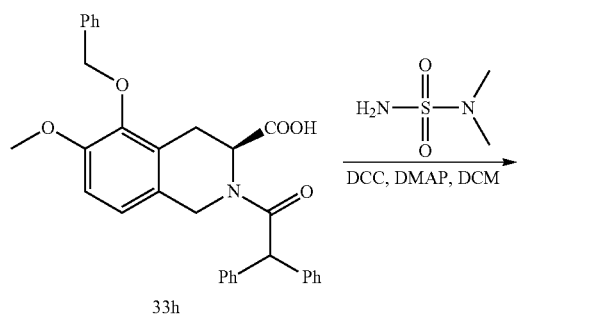

33h

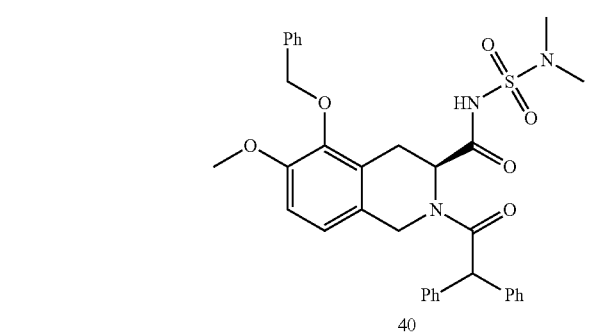

40

To a solution of compound 33h (2.50 g, 4.83 mmol) in DCM (30 mL) was added N,N-dimethyl methanesulfonamide (0.60 g, 4.83 mmol), DCC (1.20 g, 5.80 mmol) and DMAP (0.17 g, 1.45 mmol) and the mixture was stirred at RT overnight. TLC (DCM:MeOH=20:1) showed that most of the starting material was consumed. The mixture was washed with a saturated aqueous NaHCO$_3$ solution (30 mL), brine (30 mL×2), dried over Na$_2$SO$_4$, filtered and concentrated in vacuo. The residue was purified by chromatography (PE:EA=1:0 to 3:1) to give compound 40 (1.68 g, 55%) as a white solid. LC-MS (Agilent, SYN-LCMS-P-2): R$_t$ 3.16 min; m/z calculated for C$_{34}$H$_{35}$N$_3$O$_6$S [M+H]$^+$ 614.2. found [M+H]$^+$ 614.3. HPLC (JULY-L) (214 and 254 nm): R$_t$ 9.22 min.

Example 4: Preparation of Compound 41

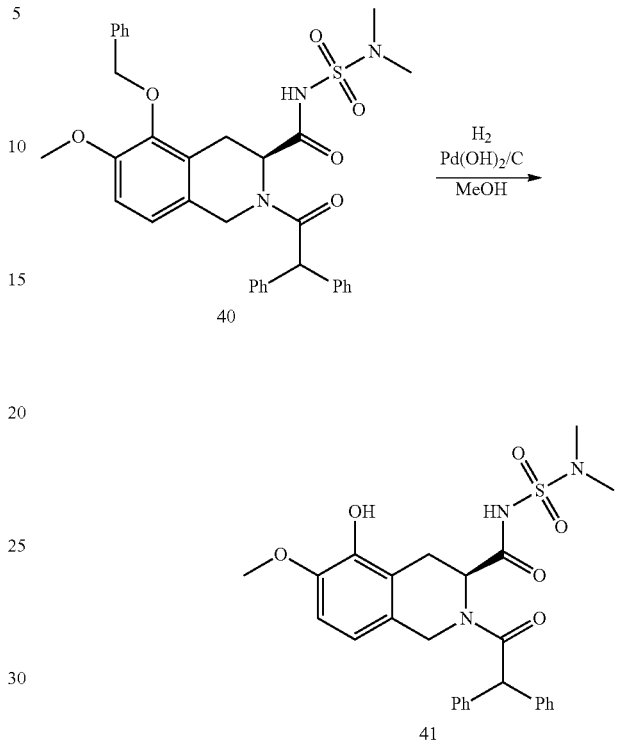

A mixture of compound 40 (1.50 g, 2.44 mmol) and 10% Pd(OH)$_2$/C (100 mg) in MeOH (30 mL) was stirred at RT under a H$_2$ atmosphere (1 atm) overnight. TLC (PE:EA=1:2) showed that the starting material was consumed. The catalyst was removed by filtration and the filtrate was concentrated in vacuo. The residue was re-crystallized from PE/EA to give compound 41 (121 g, 95%) as a white solid. LC-MS (Agilent, SYN-LCMS-P-2): R$_t$ 3.00 min; m/z calculated for C$_{27}$H$_{29}$N$_3$O$_6$S [M+H]$^+$ 524.2, [M+Na]$^+$ 546.2. found [M+H]$^+$ 524.2, [M+Na]$^+$ 546.2. HPLC (JULY-L) (214 and 254 nm): R$_t$ 8.89 min.

Example 5: Preparation of Compound 48

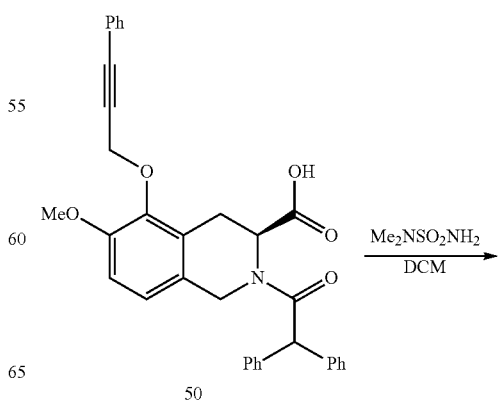

50

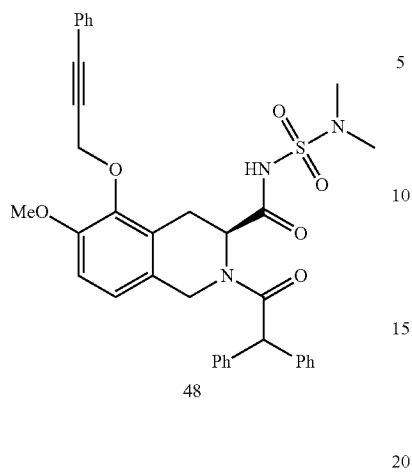

48

A mixture of compound 50 (150 mg, 0.27 mmol), N,N-dimethylsulfamide (41 mg, 0.33 mmol), DMAP (10 mg, 0.08 mmol) and DCC (68 mg, 0.33 mmol) in DCM (3 mL) was stirred at RT overnight, TLC (DCM:MeOH=10:1) showed that most of the starting material was consumed. The mixture was diluted with DCM (30 mL), washed with brine, dried over $Na_2SO_4$, filtered and concentrated in vacuo. The residue was purified by chromatography (DCM:MeOH=1:0 to 50:1) to give compound 48 (75 mg, 43%) as a white solid LC-MS (Agilent, SYN-LCMS-P-2): $R_t$ 2.89 min: m/z calculated for $C_{36}H_{35}N_3O_6S$ $[M+H]^+$ 638.2, $[M+Na]^+$ 660.2. found $[M+H]^+$ 638.3, $[M+Na]^+$ 660.3. HPLC (JULY-L) (214 and 254 nm): $R_t$ 9.59 min.

Example 6: Preparation of Compound 49

49

A mixture of compound 51 (70 mg, 0.127 mmol), N,N-dimethylsulfamide (19 mg, 0.153 mmol), DMAP (5 mg, 0.038 mmol) and DCC (32 mg, 0.153 mmol) in DCM (1 mL) was stirred at RT overnight, TLC (DCM:MeOH=10:1) showed that most of the starting material was consumed. The mixture was diluted with DCM (30 mL), washed with brine, dried over $Na_2SO_4$, filtered and concentrated in vacuo. The residue was purified by preparative HPLC to give Compound 49 (40 mg, 48%) as a white solid. LC-MS (Agilent, SYN-LCMS-P-2): $R_t$ 2.95 min; m/z calculated for $C_{36}H_{34}FN_3O_6S$ $[M+H]^+$ 656.2, $[M+Na]^+$ 678.2. found $[M+H]^+$ 656.2, $[M+Na]^+$ 678.2. HPLC (JULY-L) (214 and 254 nm): $R_t$ 9.597 min.

Example 7: Preparation of Compound 50

1. Procedure for the Preparation of Compound 50a

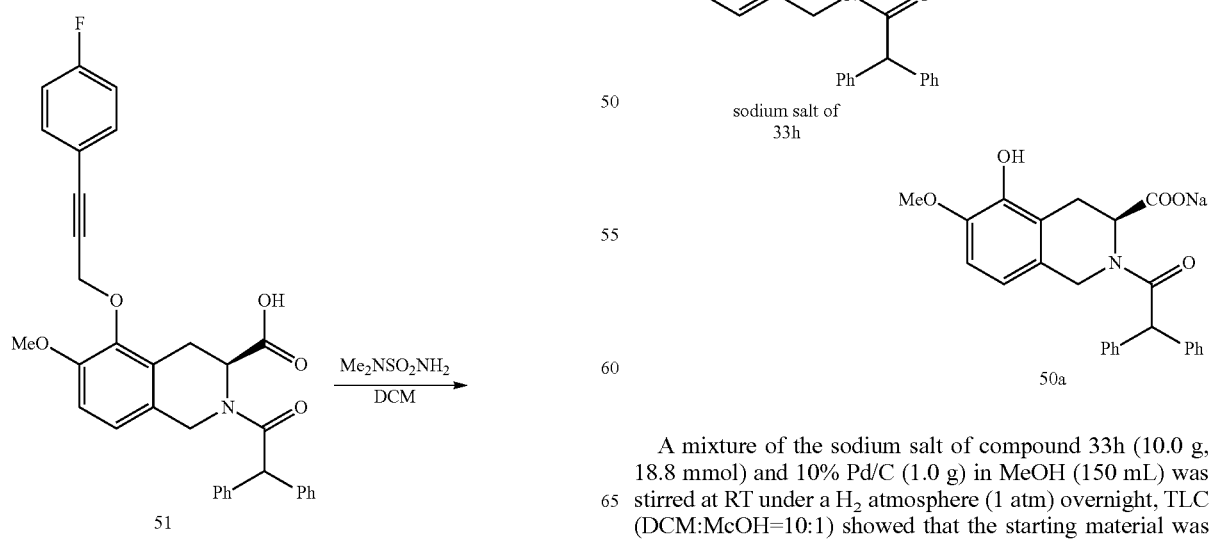

A mixture of the sodium salt of compound 33h (10.0 g, 18.8 mmol) and 10% Pd/C (1.0 g) in MeOH (150 mL) was stirred at RT under a $H_2$ atmosphere (1 atm) overnight, TLC (DCM:McOH=10:1) showed that the starting material was consumed. The mixture was filtered and the filtrate was concentrated in vacuo to give compound 50a (8.5 g, 117%) as a white solid, which was used in the next step without purification. LC-MS (Agilent, SYN-LCMS-P-2): $R_t$ 2.97 min; m/z calculated for $C_{25}H_{23}NO_5$ [M+H]$^+$ 418.2, [M+Na]$^+$ 440.2. found [M+H]$^+$ 418.2, [M+Na]$^+$ 440.1.

2. Procedure for the Preparation of Compound 50b

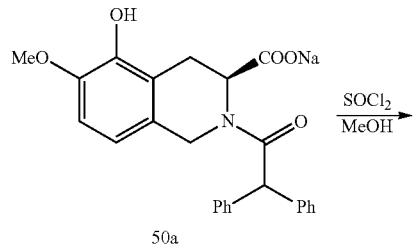

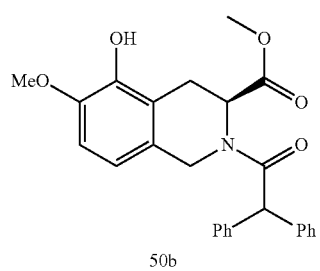

To a stirred solution of compound 50a (2.00 g, 4.55 mmol) in MeOH (30 mL) was added SOCl$_2$ (0.5 mL) and the mixture was heated at reflux for 3 h, TLC (DCM:MeOH=10:1) showed that the starting material was consumed. The mixture was cooled to RT, concentrated in vacuo and the residue was partitioned between EA and water. The organic layer was separated, washed with a saturated aqueous NaHCO$_3$ solution then brine, dried over Na$_2$SO$_4$, filtered and concentrated in vacuo to give compound 50b (1.98 g, 100%) as a white solid. LC-MS (Agilent, SYN-LCMS-P-2): $R_t$ 3.01 min; m/z calculated for $C_{2-6}H_{25}NO_5$ [M+H]$^+$ 432.2, [M+Na]$^+$ 454.2. found [M+H]$^+$ 432.2, [M+Na]$^+$ 454.2.

3. Procedure for the Preparation of Compound 50c

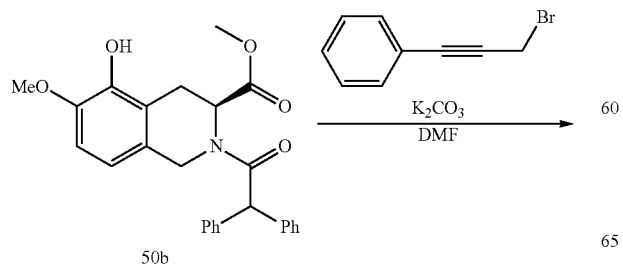

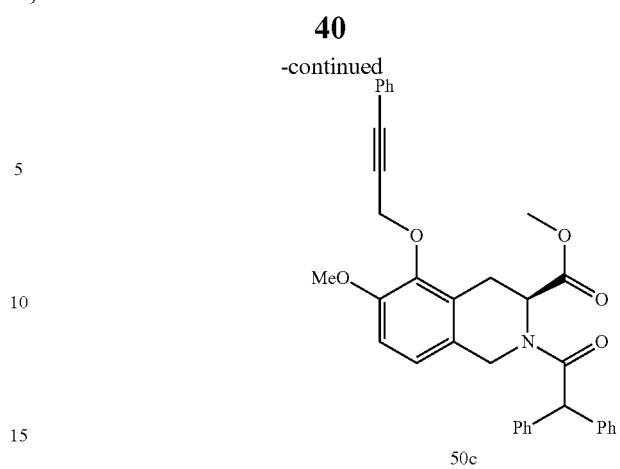

A mixture of compound 50b (300 mg, 0.69 mmol), 1-(3-bromoprop-1-ynyl)benzene (163 mg, 0.83 mmol) and K$_2$CO$_3$ (143 mg, 1.04 mmol) in DMF (10 mL) was heated at 50° C. overnight, TLC (PE:EA=1:1) showed that the starting material was consumed. The mixture was cooled to RT, poured into ice-water (100 mL) and extracted with ether (30 mL×3). The combined organic extracts were washed with brine, dried over Na$_2$SO$_4$, filtered and concentrated in vacuo. The residue was purified by chromatography (PE:EA=1:0 to 4:1) to give compound 50c (270 mg, 71%) as a white solid. LC-MS (Agilent, SYN-LCMS-P-2): $R_t$ 3.26 min; m/z calculated for $C_{35}H_{31}NO_5$ [M+H]$^+$ 546.2. found [M+H]$^+$ 546.2.

4. Procedure for the Preparation of Compound 50

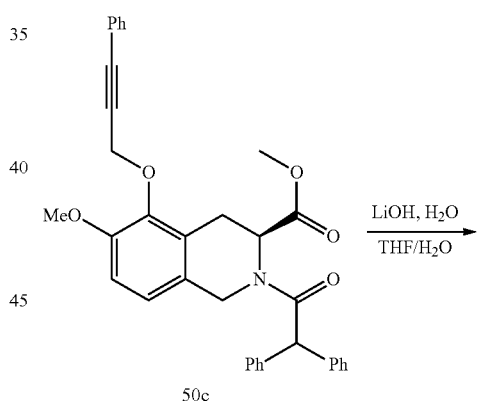

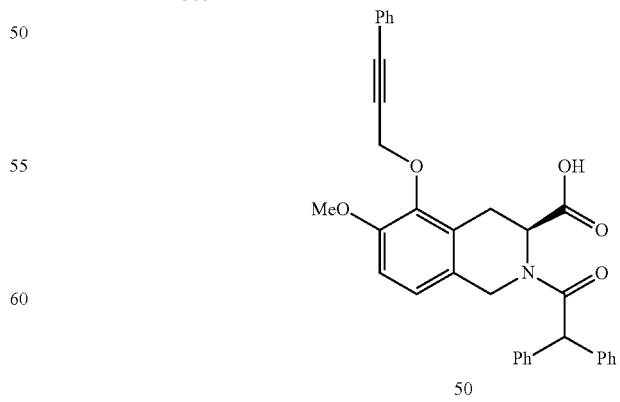

A mixture of compound 50c (270 mg, 0.49 mmol) and LiOH.H$_2$O (79 mg, 1.88 mmol) in THF/H$_2$O (3 mL/1 mL)

was stirred at RT overnight. TLC (PE:EA=1:1) showed that the starting material was consumed. The mixture was concentrated in vacuo to remove the THF and the residue was dissolved in water (30 mL) and acidified to pH~4 with a 3 M aqueous HCl solution. The resulting precipitate was collected by filtration and the obtained solid was dissolved in DCM, washed with brine, dried over $Na_2SO_4$, filtered and concentrated in vacuo. The residue was re-crystallized form PE/EA to give compound 50 (210 mg, 80%) as a white solid. LC-MS (Agilent, SYN-LCMS-P-2): $R_t$ 2.81 min; m/z calculated for $C_{34}H_{29}NO_5$ [M+H]$^+$ 532.2. found [M+H]$^+$ 532.2. HPLC (JULY-L) (214 and 254 nm): $R_t$ 9.63 min.

Example 8: Preparation of Compound 51

1. Procedure for the Preparation of Compound 51a

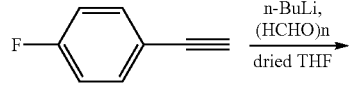

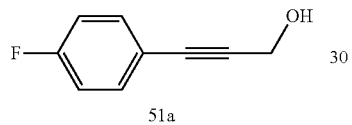
51a

To a stirred solution of 4-fluorophenylacetylene (5.0 g, 41.7 mmol) in THF (30 mL) at −65° C. under a $N_2$ atmosphere was added n-BuLi (2.5 M in hexane, 18.3 mL, 45.8 mmol) and the mixture was stirred at −65° C. for 1 h. Paraformaldehyde (2.5 g, 83.3 mmol) was added and the mixture was allowed to warm slowly to RT and stirred overnight, TLC (PE:EA=4:1) showed that the starting material was consumed. Water was added and the mixture was extracted with EA (30 mL). The organic extract was washed with water (20 mL×2), brine (20 mL), dried over $Na_2SO_4$, filtered and concentrated in vacuo to give compound 51a (6.5 g, 100%) as a brown oil which was used in next step directly.

2. Procedure for the Preparation of Compound 51b

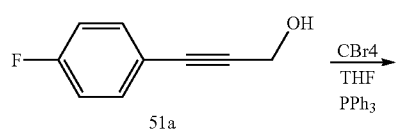

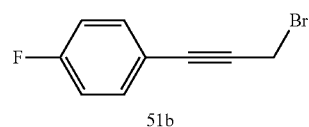
51b

To a solution of compound 51a (1.0 g, 6.67 mmol) in THF (15 mL) was added $PPh_3$ (1.92 g, 7.34 mmol) then $CBr_4$ (2.21 g, 6.67 mmol) and the mixture was stirred at RT overnight, TLC (PE:EA=4:1) showed that the starting material was consumed. PE (30 mL) was added and the mixture was filtered. The filtrate was concentrated in vacuo and the residue was purified by chromatography (100% PE) to give compound 51b (1.5 g, 100%) as a colorless oil.

3. Procedure for the Preparation of Compound 51c

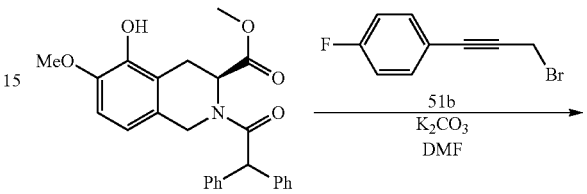

51c

A mixture of compound 50b (300 mg, 0.69 mmol), compound 51b (177 mg, 0.83 mmol) and $K_2CO_3$ (143 mg, 1.04 mmol) in DMF (10 mL) was heated at 50° C. overnight, TLC (PE:EA=1:1) showed that the starting material was consumed. The mixture was cooled to RT, poured into ice-water (80 mL) and extracted with ether (30 mL×3). The combined organic extracts were washed with brine, dried over $Na_2SO_4$, filtered and concentrated in vacuo. The residue was purified by chromatography (PE:EA=1:0 to 4:1) to give compound 51c (280 mg, 72%) as a white solid. LC-MS (Agilent, SYN-LCMS-P-2): $R_t$ 3.41 min; m/z calculated for $C_{35}H_{30}FNO_5$ [M+H]$^+$ 564.2, [M+Na]$^+$ 586.2. found [M+H]$^+$ 564.2, [M+Na]$^+$ 586.2.

4. Procedure for the Preparation of Compound 51

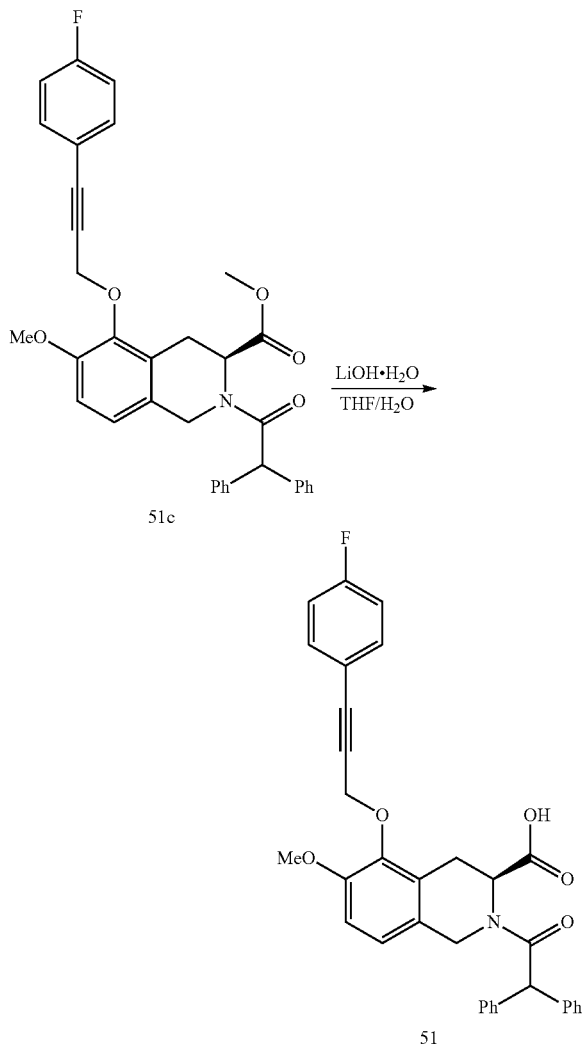

A mixture of compound 51c (280 mg, 0.49 mmol) and LiOH.H$_2$O (63 mg, 1.49 mmol) in THF/H$_2$O (3 mL/1 mL) was stirred at RT overnight, TLC (PE:EA=1:1) showed that the starting material was consumed. The mixture was concentrated in vacuo to remove the THF and the residue was dissolved in water (30 mL), acidified to pH~3 with 3 M aqueous HCl solution and extracted with DCM. The organic extracts were washed with brine, dried over Na$_2$SO$_4$, filtered and concentrated in vacuo. The residue was purified by chromatography (DCM:MeOH=1:0 to 100:1) to give compound 51 (120 mg, 44%) as a white solid. LC-MS (Agilent, SYN-LCMS-P-2): R$_t$ 3.48 min; m/z calculated for C$_{34}$H$_{28}$FNO$_5$ [M+H]$^+$ 550.2, [M+Na]$^+$ 572.2. found [M+H]$^+$ 550.2, [M+Na]$^+$ 572.2. HPLC (JULY-L) (214 and 254 nm): R$_t$ 9.64 min.

Biological Example 1: AT$_2$ Receptor Binding

Media and Solutions
1. Trypsin-EDTA (for preparation of 100 mL)
   Trypsin 0.25 g
   2% EDTA 2 mL
   PBS 98 mL
   Dissolve trypsin in 2% EDTA and PBS completely; sterilize the solution by passing through a 0.20 μM membrane filter; store at 4° C.
2. DMEM medium (for preparation of IL)
   The powder was dissolved into 950 mL of distilled water with gentle stirring until the solution becomes clear.
   Add NaHCO$_3$ 1.176 g for DMEM medium.
   Adjust pH of medium to 0.2-0.3 below final working pH using 1 M NaOH or 1 M HCl. Add slowly with stirring.
   Dilute to 1 liter with ddH$_2$O.
   Sterilize the medium immediately by filtration.
   Store at 4° C.
3. TE buffer
   20 mM Tris-HCl, pH 7.4.
   5 mM EDTA
4. Binding Assay Buffer
   50 mM HEPES, pH 7.4
   5 mM MgCl$_2$
   1 mM CaCl$_2$
   0.2% BSA
5. Wash Buffer
   50 mM Hepes, pH 7.4

Procedures for HEK293/AT$_2$ Receptor Transient Cell Transfection
   Cells were plated into 150 mm dish at 50% density for transient transfection. Cells were ready for transfection after overnight incubation (the confluence reaches around 80%).
   75 μL Lipofectamine™ 2000 diluted in 6.25 mL OptiMEM I Reduced Serum Medium, was mixed gently, and incubated at room temperature for 5 minutes, 50 μg expression plasmid DNA diluted in 6.25 mL OptiMEM I Reduced Serum Medium without serum was mixed gently.
   After the 5 minute incubation, the diluted DNA was combined with the diluted Lipofectamine™ 2000 (total volume is 12.5 mL). The mixture was mixed gently and incubated for 30 minutes at room temperature to allow the DNA-Lipofectamine™ 2000 complexes to form.
   The 12.5 mL DNA-Lipofectamine™ 2000 complexes were added into the 150 mm dish and mixed gently by rocking the dish back and forth.
   The cells were incubated at 37° C. with 5% CO$_2$ for 48 hours.
   Cells were collected and stored frozen at −80° C.

Procedures for HEK293/AT$_2$ Receptor Cell Membrane Preparation
   Frozen HEK293/AT$_2$ receptor (transient transfected) cells were homogenized in ice cold TE buffer for 10 s.
   The homogenate was centrifuged at 25,000 g for 30 minutes.
   The pellet was resuspended in ice cold tissue buffer.
   Protein concentrations were determined using Bradford assay method with BSA as standard.
   The membrane protein was frozen under −80° C.

Compound Preparation
   Solutions of all compounds were prepared by microplate liquid handling equipment such as Janus or Precision 2000. Compounds, dissolved in DMSO were stored in a Freezer. Compounds were prepared from 30 mM in 100% DMSO.

Step 1: Dose Plate Preparation (96 Well Plate)
   Add the 3 μL [30 mM] compound stock to column 1 on the plate.
   Add 15 μL of 100% DMSO to column 1.
   Add 10.81 μL of 100% DMSO to column 2-12.

Transfer 5 µL from column 1 into column 2 (half log dilution).
Transfer 5 µL from column 2 into column 3 (half log dilution).
Transfer 5 µL from column 3 into column 4 (half log dilution).
Transfer 5 µL from column 4 into column 5 (half log dilution).
Transfer 5 µL from column 5 into column 6 (half log dilution).
Transfer 5 µL from column 6 into column 7 (half log dilution).
Transfer 5 µL from column 7 into column 8 (half log dilution).
Transfer 5 µL from column 8 into column 9 (half log dilution).
Transfer 5 µL from column 9 into column 10 (half log dilution)
Transfer 5 µL from column 10 into column 11 (half log dilution)
Transfer 5 µL from column 11 into column 12 (half log dilution).

All the compounds were diluted using Precision 2000 microplate liquid handling equipment. The top concentration of compound was 5 mM with 100% DMSO.

Step 2: Working Plate Preparation (96 Well Plate)
Compounds were diluted 50-fold with buffer.
49 µL buffer was added to the well of 96 well plate.
1 µL compound solution from dose plate was transferred to the corresponding well of working plate.
The top concentration of compound was 100 µM with 2% DMSO.

Step 3: Assay Plate Preparation (96 Well Plate)
15 µL of compound solution was transferred from each well of working plate to the well of assay plate by Janus. Each compound was assayed in duplicate in each plate and there were 4 compounds per plate.

Procedures for $AT_2$ Receptor Binding Assay
120 µL membrane (5 mg protein/well) was incubated with 15 µL of [$^{125}$I]-CGP42112A and 15 µL of compound at RT for 1.5 hrs.
The binding reaction was stopped by rapid filtration through Unifilter GF/C plates (presoaked in 0.3% (v:v) BSA).
Plate was washed three times with ice cold wash buffer.
The filtration plates were dried at 37° C. overnight.
50 µL of scintillation cocktail was added to each well.
Radioactivity was determined using MicroBetaTriluxmicroplate scintillation counter.

Data Analysis
Data was analyzed through 4 parameter logic using Prism 5.0 software.
The results are shown in the following Table:

| Compound | IC$_{50}$ (nM) |
|---|---|
| 33 | 431.3 |
| 34 | 33.54 |
| 40 | 10.86 |
| 41 | 1793 |
| 48 | 79.53 |
| 49 | 205.8 |
| 50 | 96.15 |
| 51 | 133.2 |

REFERENCES

Anand et al., 2012, Angiotensin II Type 2 receptor (AT$_2$R) localisation and antagonist-mediated inhibition of capsaicin responses and neurite outgrowth in human and rat sensory neurons, *Eur. J Pain,* 17(7):1012-1026.

Burk et al., 1993. Preparation and use of C$_2$-symmetric bis(phospholanes): production of α-amino acid derivatives via highly enantioselective hydrogenation reactions, *J. Am. Chem. Soc.,* 115:10125-10138.

Chakrabarty et al., 2008, Estrogen elicits dorsal root ganglion axon sprouting via a rennin-angiotensin system. *Endocrinology.* 149(7):3452-3460.

Chakrabarty et al., 2013, Angiotensin II Receptor Type 2 activation is required for cutaneous sensory hypersensitivity in a rat hind paw model of inflammatory pain, *J. Pain.* www.jpain.org/article/51526-5900(13)00959-0/full text.

Clere et al., 2010, Deficiency or blockade of angiotensin II type 2 receptor delays tumorigenesis by inhibiting malignant cell proliferation and angiogenesis. *Int. J. Cancer,* 127: 2279-2291.

Izu et al., 2009, Angiotensin II Type 2 receptor blockade increases bone mass. *J. Biol. Chem.,* 284(8):4857-4864.

Smith, Woodruff et al., 2013, A small molecule Angiotensin II Type 2 Receptor (AT$_2$R) antagonist produces analgesia in a rat model of neuropathic pain by inhibition of p38 mitogen-activated protein kinase (MAPK) and p44/p42 MAPK activation in the dorsal rood ganglia, *Pain Medicine,* in press, doi:10.1111/pme.12157.

Smith et al., 2013, Small molecule angiotensin II Type 2 receptor (AT$_2$R) antagonists as novel analgesics for neuropathic pain: Comparative pharmacokinetics, radioligand binding and efficacy in rats; *Pain Medicine,* 14(5): 692-705.

Steckelings et al., 2005, The AT$_2$ receptor —A matter of love and hate. *Peptides,* 26:1401-1409.

Wallinder et al., 2008, Selective angiotensin II AT$_2$ receptor agonists; Benzamide structure-activity relationships. *Bioorganic & Medicinal Chemistry,* 16:6841-6849.

Wan et al., 2004, Design, Synthesis and biological evaluation of the first selective nonpeptide AT$_2$ receptor agonist. *J. Med. Chem.,* 47:5995-6008.

Wexler et al., 1996. Nonpeptide angiotensin II receptor antagonists: The next generation in antihypertensive therapy. *J. Med. Chem.,* 39(3):325-656.

The invention claimed is:
1. A compound of formula (I):

wherein R$_1$ is —C(=O)CHR$_6$R$_7$;
R$_2$ is a carboxylic acid, —C(=O)-2-glucuronic acid, or —C(O)NHSO$_2$N(C$_{1-6}$alkyl)$_2$;
R$_4$ is R$_9$, —C$_{1-6}$alkylR$_9$, —C$_{2-6}$alkenylR$_9$, —C$_{2-6}$alkynylR$_9$, —OH, —OR$_9$, —OC$_{1-6}$alkylR$_9$, —OC$_{2-6}$alkenylR$_9$, —OC$_{2-6}$alkynylR$_9$, —NHC(=O)R$_9$, —NHC(=O)C$_{1-6}$alkylR$_9$, —NHC(=O)C$_{2-6}$alkenylR$_9$, —NHC(=O)C$_{2-6}$alkynylR$_9$, —NHC(=O)NHR$_9$, —NHC(=O)NHC$_{1-6}$alkylR$_9$, —NHC(=O)NHC$_{2-6}$alkenylR$_9$, —NHC(=O)NHC$_{2-6}$alkynylR$_9$, —NHC(=O)OR$_9$, —NHC(=O)OC$_{1-6}$alkylR$_9$, —NHC(=O)OC$_{2-6}$alkenylR$_9$, —NHC(=O)OC$_{2-6}$alkynylR$_9$, —NHSO$_2$R$_9$, —NHSO$_2$C$_{1-6}$alkylR$_9$, —NHSO$_2$C$_{2-6}$alkenylR$_9$, —NHSO$_2$C$_{2-6}$alkynylR$_9$, —SO$_2$NHR$_9$, —SO$_2$NHC$_{1-6}$alkylR$_9$, —SO$_2$NHC$_{2-6}$alkenylR$_9$, —SO$_2$NHC$_{2-6}$alkynylR$_9$, —C(=O)NHR$_9$, —C(=O)NHC$_{1-6}$alkylR$_9$, —C(=O)NHC$_{2-6}$alkenylR$_9$, —C(=O)NHC$_{2-6}$alkynylR$_9$, —C(=O)R$_9$, —C(=O)C$_{1-6}$alkylR$_9$, —C(=O)C$_{2-6}$alkenylR$_9$, —C(=O)C$_{2-6}$alkynylR$_9$, —C(=O)OR$_9$, —C(=O)OC$_{1-6}$alkylR$_9$, —C(=O)OC$_{2-6}$alkenylR$_9$, —C(=O)OC$_{2-6}$alkynylR$_9$, —C(=O)NHR$_9$, —C(=O)NHC$_{1-6}$alkylR$_9$, —C(=O)NHC$_{2-6}$alkenylR$_9$ or —C(=O)NHC$_{2-6}$alkynylR$_9$;

$R_3$ is hydrogen;

$R_5$ is —OH, —C$_{1-6}$alkyl, —OC$_{1-6}$alkyl, —C(R$_{10}$)$_3$, —OC(R$_{10}$)$_3$, aryl, —C$_{1-6}$alkylaryl or —OC$_{1-6}$alkylaryl;

$R_6$ and $R_7$ are aryl;

$R_8$ is hydrogen, —C$_{1-6}$alkyl, aryl or —C$_{1-6}$alkylaryl;

$R_9$ is cycloalkyl, cycloalkenyl, aryl, heterocyclyl or heteroaryl;

each $R_{10}$ is independently selected from the group consisting of hydrogen and halogen; and wherein each alkyl, alkenyl, alkynyl, cycloalkyl, cycloalkenyl, aryl, heterocyclyl and heteroaryl may be optionally substituted with one or more optional substituents selected from the group consisting of C$_{1-6}$alkyl, C$_{2-6}$alkenyl, C$_{3-6}$cycloalkyl, oxo, —OH, —SH, C$_{1-6}$alkylO—, C$_{2-6}$alkenylO—, C$_{3-6}$cycloalkylO—, C$_{1-6}$alkylS—, C$_{2-6}$alkenylS—, C$_{3-6}$cycloalkylS—, —CO$_2$H, —CO$_2$C$_{1-6}$alkyl, —NH$_2$, —NH(C$_{1-6}$alkyl), —N(C$_{1-6}$alkyl)$_2$, —NH(phenyl), —N(phenyl)$_2$, —N(C$_{1-6}$alkyl)(phenyl), —CN, —NO$_2$, -halogen, —CF$_3$, —OCF$_3$, —SCF$_3$, —CHF$_2$, —OCHF$_2$, —SCHF$_2$, -phenyl, -heterocyclyl, -heteroaryl, -Oheteroaryl, -Oheterocyclyl, -Ophenyl, —C(O)phenyl and —C(O)C$_{1-6}$alkyl;

or a pharmaceutically acceptable salt thereof;

provided that:

when $R_2$ is —CH$_2$OH, CO$_2$H or a carboxylic acid bioisostere and $R_4$ is phenyl, -Ophenyl, —C$_{1-4}$alkylphenyl or —OC$_{1-4}$alkylphenyl in which the alkyl group is unsubstituted, biphenyl, -Obiphenyl, naphthyl or -Onaphthyl, $R_5$ is not —OC$_{1-6}$alkyl, phenyl, benzyl, naphthyl, biphenyl or -Oaryl.

2. A compound according to claim 1 wherein $R_1$ is —C(=O)CH(phenyl)(phenyl), or a pharmaceutically acceptable salt thereof.

3. A compound according to claim 1 wherein $R_2$ is —CO$_2$H or —C(=O)NHSO$_2$N(C$_{1-4}$alkyl)$_2$, or a pharmaceutically acceptable salt thereof.

4. A compound according to claim 1 wherein $R_4$ is —OH, -aryl, -heterocyclyl, -heteroaryl, —C$_{1-6}$alkylaryl, —OC$_{1-6}$alkylaryl, —C$_{2-6}$alkenylaryl, —OC$_{2-6}$alkenylaryl, —C$_{2-6}$alkynylaryl, —OC$_{2-6}$alkynylaryl, —SO$_2$NHaryl, —SO$_2$NHC$_{1-6}$alkylaryl, —SO$_2$NHC$_{2-6}$alkenylaryl, —SO$_2$NHC$_{2-6}$alkynylaryl, —NHSO$_2$aryl —NHSO$_2$C$_{1-6}$alkylaryl, —NHSO$_2$C$_{2-6}$alkenylaryl, —NHSO$_2$C$_{2-6}$alkynylaryl, —NHC(=O)NHaryl, —NHC(=O)NHC$_{1-6}$alkylaryl, —NHC(=O)NHC$_{2-6}$alkenylaryl, —NHC(=O)NHC$_{2-6}$alkynylaryl, —NHCO$_2$aryl, —NHCO$_2$C$_{1-6}$alkylaryl, —NHCO$_2$C$_{2-6}$alkenylaryl, or —NHCO$_2$C$_{2-6}$alkynylaryl, wherein each alkyl, alkenyl, alkynyl, aryl, heterocyclyl and heteroaryl is optionally substituted with one or more optional substituents selected from the group consisting of C$_{1-6}$alkyl, C$_{2-6}$alkenyl, C$_{3-6}$cycloalkyl, oxo (=O), —OH, —SH, C$_{1-6}$alkylO—, C$_{2-6}$alkenylO—, C$_{3-6}$cycloalkylO—, C$_{1-6}$alkylS—, C$_{2-6}$alkenylS—, C$_{3-6}$cycloalkylS—, —CO$_2$H, —CO$_2$C$_{1-6}$alkyl, —NH$_2$, —NH(C$_{1-6}$alkyl), —N(C$_{1-6}$alkyl)$_2$, —NH(phenyl), —N(phenyl)$_2$, —N(C$_{1-6}$alkyl)(phenyl), —CN, —NO$_2$, -halogen, —CF$_3$, —OCF$_3$, —SCF$_3$, —CHF$_2$, —OCHF$_2$, —SCHF$_2$, -phenyl, -heterocyclyl, -heteroaryl, -Oheteroaryl, -Oheterocyclyl, -Ophenyl, —C(O)phenyl and —C(O)C$_{1-6}$alkyl, or a pharmaceutically acceptable salt thereof.

5. A compound according to claim 4 wherein $R_4$ is phenyl, benzoxazole, 4-phenyloxazole, 1-piperidine, 4-phenyl-1-piperidine, —C$_{1-6}$alkylphenyl, —OC$_{1-6}$alkylphenyl, —C$_{2-6}$alkenylphenyl, —OC$_{2-6}$alkenylphenyl, —C$_{2-6}$alkynylphenyl, —OC$_{2-6}$alkynylphenyl, —SO$_2$NHphenyl, —SO$_2$NHC$_{1-6}$alkylphenyl, —SO$_2$NHC$_{2-6}$alkenylphenyl, —SO$_2$NHC$_{2-6}$alkynylphenyl, —NHSO$_2$phenyl —NHSO$_2$C$_{1-6}$alkylphenyl, —NHSO$_2$C$_{2-6}$alkenylphenyl, —NHSO$_2$C$_{2-6}$alkynylphenyl, —NHC(=O)NHphenyl, —NHC(=O)NHC$_{1-6}$alkylphenyl, —NHC(=O)NHC$_{2-6}$alkenylphenyl, —NHC(=O)NHC$_{2-6}$alkynylphenyl, —NHCO$_2$phenyl, —NHCO$_2$C$_{1-6}$alkylphenyl, —NHCO$_2$C$_{2-6}$alkenylphenyl, or —NHCO$_2$C$_{2-6}$alkynylphenyl, or a pharmaceutically acceptable salt thereof.

6. A compound according to claim 5 wherein $R_4$ is phenyl, benzoxazole, 4-phenyloxazole, 1-piperidine, 4-phenyl-1-piperidine, —C$_{1-3}$alkylphenyl, —OC$_{1-3}$alkylphenyl, —C$_{2-3}$alkenylphenyl, —OC$_{2-3}$alkenylphenyl, —C$_{2-3}$alkynylphenyl, —OC$_{2-3}$alkynylphenyl, —SO$_2$NHphenyl, —SO$_2$NHC$_{1-3}$alkylphenyl, —SO$_2$NHC$_{2-3}$alkenylphenyl, —SO$_2$NHC$_{2-3}$alkynylphenyl, —NHSO$_2$phenyl —NHSO$_2$C$_{1-3}$alkylphenyl, —NHSO$_2$C$_{2-3}$alkenylphenyl, —NHSO$_2$C$_{2-3}$alkynylphenyl, —NHC(=O)NHphenyl, —NHC(=O)NHC$_{1-3}$alkylphenyl, —NHC(=O)NHC$_{2-3}$alkenylphenyl, —NHC(=O)NHC$_{2-3}$alkynylphenyl, —NHCO$_2$phenyl, —NHCO$_2$C$_{1-3}$alkylphenyl, —NHCO$_2$C$_{2-3}$alkenylphenyl or —NHCO$_2$C$_{2-3}$alkynylphenyl, or a pharmaceutically acceptable salt thereof.

7. A compound according to claim 1 wherein $R_5$ is —OH, —OC$_{1-6}$alkyl or —OC(R$_{10}$)$_3$, or a pharmaceutically acceptable salt thereof.

8. A compound according to claim 7 wherein $R_5$ is —OH, —OCH$_3$, —OCF$_3$ or —OCHF$_2$, or a pharmaceutically acceptable salt thereof.

9. A compound of Formula (I) according to claim 1 selected from the group consisting of:

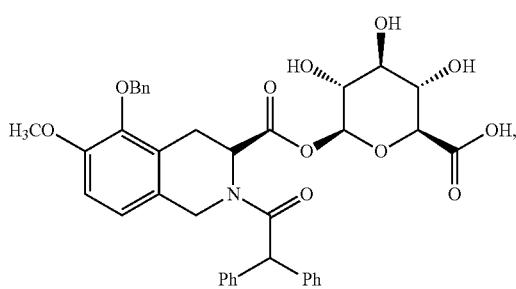

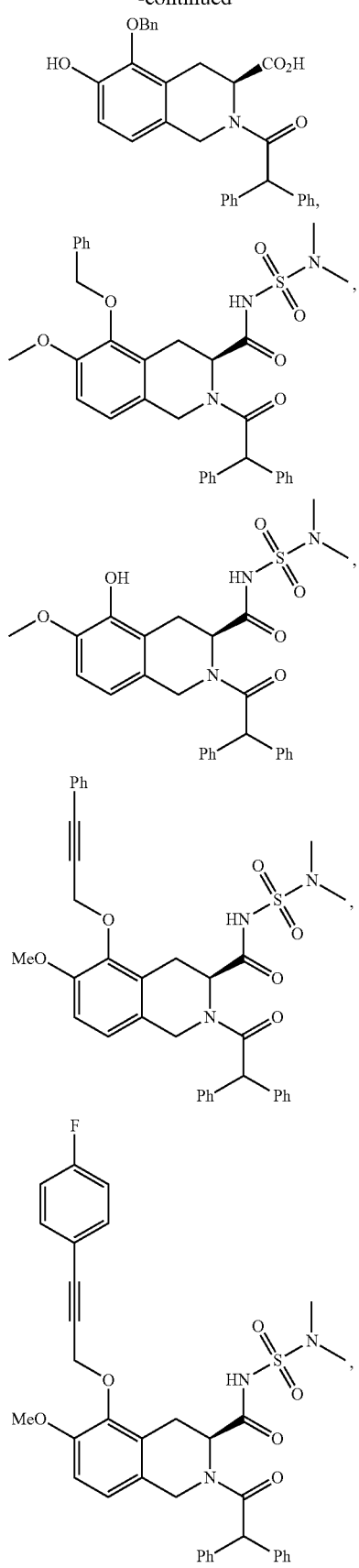
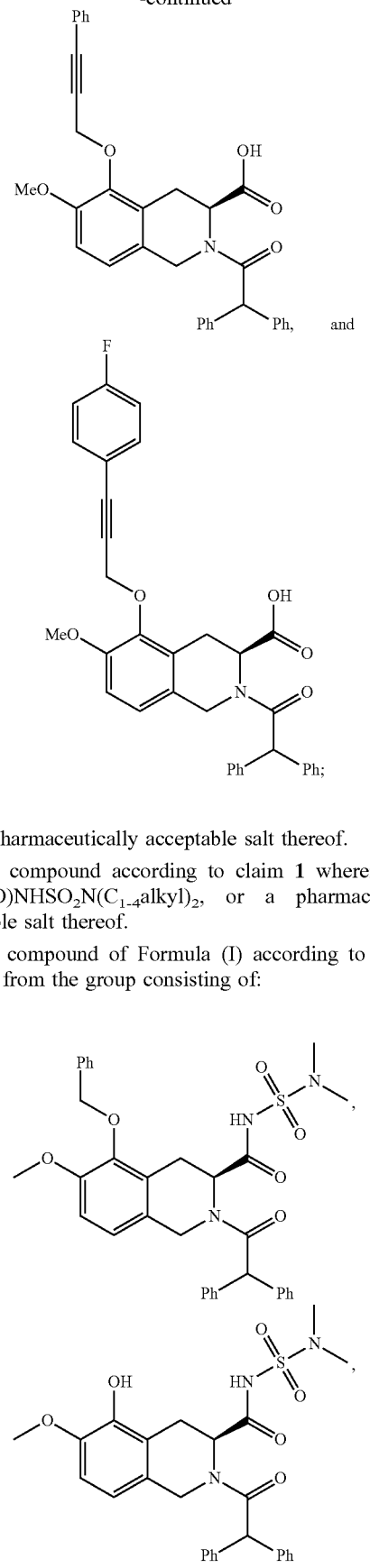
or a pharmaceutically acceptable salt thereof.
10. A compound according to claim 1 wherein $R_2$ is —C(=O)NHSO$_2$N(C$_{1-4}$alkyl)$_2$, or a pharmaceutically acceptable salt thereof.
11. A compound of Formula (I) according to claim 1 selected from the group consisting of:

-continued

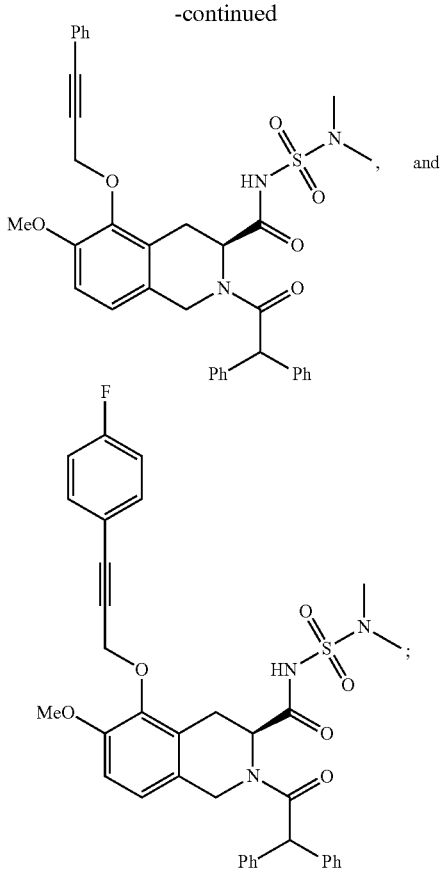

or a pharmaceutically acceptable salt thereof.

12. A pharmaceutical composition comprising a compound of formula (I) according to claim 1 or a pharmaceutically acceptable salt thereof and a pharmaceutically acceptable carrier.

13. A pharmaceutical composition comprising a compound according to claim 9 or a pharmaceutically acceptable salt thereof and a pharmaceutically acceptable carrier.

14. A pharmaceutical composition comprising a compound according to claim 11 or a pharmaceutically acceptable salt thereof and a pharmaceutically acceptable carrier.

15. A method of treating neuropathic pain in a subject comprising administering a compound of formula (I) according to claim 1 or a pharmaceutically acceptable salt thereof.

16. A method or treating inflammatory pain in a subject comprising administering a compound of formula (I) according to claim 1 or a pharmaceutically acceptable salt thereof.

17. A method of treating impaired nerve conduction velocity in a subject comprising administering a compound of formula (I) according to claim 1 or a pharmaceutically acceptable salt thereof.

18. A method of producing analgesia in a subject comprising administering a compound of formula (I) according to claim 1 or a pharmaceutically acceptable salt thereof.

19. A method of treating a cell proliferative disorder in a subject comprising administering a compound of formula (I) according to claim 1 or a pharmaceutically acceptable salt thereof.

20. A method of treating a disorder associated with an imbalance between bone resorption and bone formation in a subject comprising administering a compound of formula (I) according to claim 1 or a pharmaceutically acceptable salt thereof, wherein the disorder is osteoporosis.

* * * * *